Figure 1:
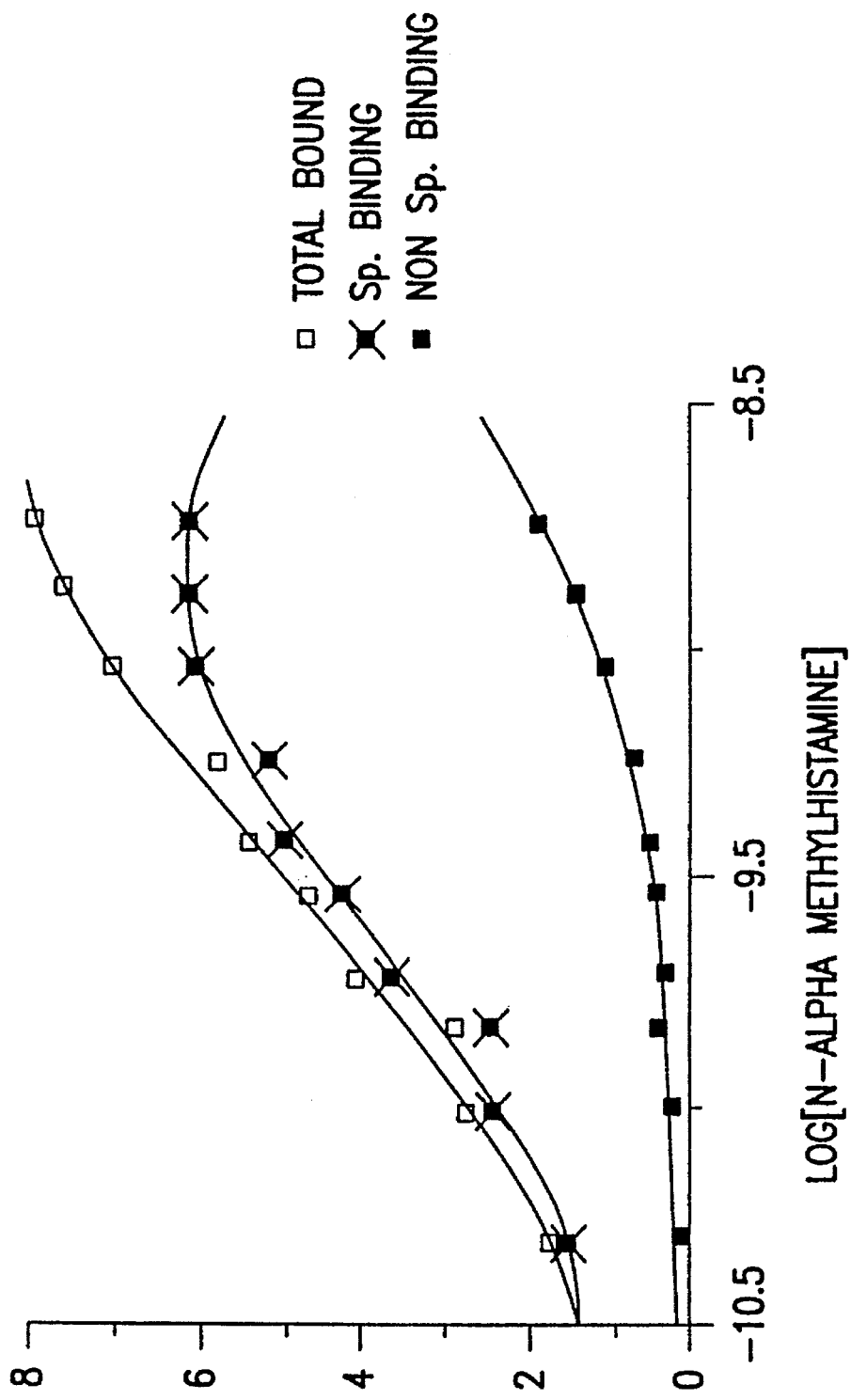

United States Patent [19]
Durant et al.

[11] Patent Number: 5,486,526
[45] Date of Patent: Jan. 23, 1996

[54] HISTAMINE H$_3$-RECEPTOR ANTAGONISTS AND THERAPEUTIC USES THEREOF

[75] Inventors: Graham J. Durant, Marshfield, Mass.; Amin M. Khan, Toledo; Clark E. Tedford, S. Russell, both of Ohio

[73] Assignees: The University of Toledo, Toledo; Gliatech, Inc., Beachwood, both of Ohio

[21] Appl. No.: 145,903

[22] Filed: Oct. 29, 1993

Related U.S. Application Data

[63] Continuation-in-part of PCT/US93/03104, Mar. 31, 1993, which is a continuation-in-part of Ser. No. 862,657, Apr. 1, 1992, abandoned.

[51] Int. Cl.$^6$ .................. C07D 411/00; C07D 211/06; C07D 233/00; A01N 43/40
[52] U.S. Cl. .................. 514/319; 546/203; 546/210; 548/314.7; 514/326; 514/397
[58] Field of Search .................. 546/203, 210; 548/314.7; 514/319, 326, 397

[56] References Cited

U.S. PATENT DOCUMENTS

| | | | |
|---|---|---|---|
| 4,220,653 | 9/1980 | Vivino | 514/400 |
| 4,707,487 | 11/1987 | Arrang et al. | 514/326 |
| 4,767,778 | 8/1988 | Arrang et al. | 514/397 |
| 5,034,539 | 7/1991 | Arrang et al. | 548/344 |
| 5,051,424 | 9/1991 | Wieriaga | 514/255 |
| 5,070,101 | 12/1991 | Kaminski | 514/399 |
| 5,290,790 | 3/1994 | Arrang et al. | 514/326 |

FOREIGN PATENT DOCUMENTS

| | | |
|---|---|---|
| 0197840 | 10/1986 | European Pat. Off. |
| 0494010A1 | 7/1992 | European Pat. Off. |
| WO91/17146 | 11/1991 | WIPO |

OTHER PUBLICATIONS

Arrang et al., 1983, Auto-inhibition of brain histamine release mediated by a novel class (H$_3$) of histamine receptor, Nature 302: 832–837.

Cooper et al., "Histamine Receptors", *Comprehensive Medical Chemistry*, vol. 3, chap. 125, pp. 323–421, Pergamon Press (1990).

Janssens et al., 1985, New Antihistaminic N–Heterocyclic 4–Piperidinamines. 3. Synthesis and Antihistaminic Activity of N–(4–Piperidinyl)–3H–imidazo [4,5–b] pyridin–2–amines, J. Med. Chem. 28: 1943–1947.

Arrang et al., 1985, Steroselectivity Of The Histamine H$_3$–Presynaptic Autoreceptor, Eur. J. Pharmacol. 117: 109–114.

Arrang et al., 1987, Highly Potent And Selective Ligands For Histamine $_3$–Receptors, Nature 327:117–123.

Arrang et al., 1988, H$_3$–Receptors Control Histamine Release In Human Brain, J. Neurochem. 51: 105–108.

Arrang et al., 1988, Intérêt Potential de Ligands Puissants et Specifiques du Recepteur H$_3$ de l'Histamine, Allergie Immunol. 20: 327–331.

Arrang et al., 1988, Highly Potent And Selective Ligands For A New Class H$_3$ of Histamine Receptor, Invest. Radiol. 23 (Suppl. 1) S130–S132.

Timmerman, 1990, Histamine H$_3$ Ligands: Just Pharmacological Tools Or Potential Therapeutic Agents, J. Med. Chem. 33: 4–11.

Schwartz et al., 1990, A Third Histamine Receptor Subtype: Characterization, Localization And Functions Of the H$_3$–Receptor, Agents And Actions 30: 13–23.

(List continued on next page.)

*Primary Examiner*—Gary L. Geist
*Assistant Examiner*—C. Harris
*Attorney, Agent, or Firm*—Pennie & Edmonds

[57] ABSTRACT

The present invention is directed to compounds of the class of piperidyl-imidazole derivative histamine H$_3$-receptor antagonists. Such compounds have affinity for histamine H$_3$-receptor, and preferably penetrate the blood-brain barrier. The compounds can block the soporific effect of an H$_3$-receptor agonist. Illustrative of the compounds of the invention is the molecule 4-(1-cyclohexylvaleroyl-4-piperidyl)-1H-imidazole. These compounds have been found to have utility in treating cognitive disorders and have been found to be useful as appetite suppressants.

9 Claims, 8 Drawing Sheets

OTHER PUBLICATIONS

West et al., 1990, Identification Of Two $H_3$–Histamine Receptor Subtypes, Mol. Pharmacol. 38: 610–613.

Lipp et al., 1991, Novel Chiral $H_3$–Receptor Agonists, In *New Perspectives in Histamine Research*, Birkhäuser Verlag: Basel, pp. 277–282.

Poli et al., 1991, Histamine $H_3$–Receptor Activation Inhibits Acetylcholine Release From The Guinea Pig Myenteric Plexus, Agents And Actionss 33: 167–169.

Bent et al., 1991, The Influence Of $H_1$, —$H_2$–and $H_3$–Receptors On The Spontaneous And Con A Induced Histamine Release From Human Adenoid Mast Cells, Agents and Actions 33: 67–70.

Ganellin et al., 1991, Synthesis of Pyridyl Isosteres Of This Peramide As $H_3$–Receptor Histamine Antagonists, Collect. Czech. Res. Commun. 56: 2448–2455.

Arrang et al., 1991, The Histamine $H_3$–Receptor: Pharmacology, Roles and Clinical Implications Studied With Agonists, in *New Perspectives in Histamine Research*, Birkhäuser Verlag: Basel, pp. 55–67.

Leurs et al., 1992, The Histamine $H_3$–Receptor: A Target for Developing New Drugs, Prog. Drug Res. 39:127–165.

Yoshimatsu et al., 1993, Abnormalities in Obese Zuckers: Defective Control of Histaminergic Functions, Physiology & Behavior 54: 487–491.

Khan et al., 1993, Synthesis and $H_3$–Receptor Affinities of Isomeric N–Methyl–and N–Benzyl–Imidazole Derivatives of Thioperamide, Med. Chem. Res. 3: 428–437.

HISTAMINE H₃-RECEPTOR ANTAGONISTS AND THERAPEUTIC USES THEREOF

The present application is a continuation-in-part of International application No. PCT/US93/03104, filed Mar. 31, 1993 which is a continuation-in-part of application Ser. No. 07/862,657, filed Apr. 1, 1992 abandoned, each of which is incorporated herein by reference in its entirety.

1. FIELD OF THE INVENTION

The present invention relates to novel compounds having potent activity as histamine $H_3$-receptor ("$H_3$") antagonists, and methods of using such compounds.

2. BACKGROUND OF THE INVENTION

Dementias tend to be characterized by cognitive disorders and often by depression. A particularly devastating dementia is Alzheimer's disease (AD). AD affects more than 30% of humans over 80 years of age, and as such, represents one of the most important health problems in developed countries (Evans et al., *J.A.M.A.* 262: 2551–2556 (1989); Katzman and Saitoh, *FASEB J.* 280: 278–286 (1991)). This neurodegenerative disorder of unknown etiology is clinically characterized by gradual impairment of cognitive function. The large buildup of intracytoplasmic neurofibrillary tangles and neurite plaques observed histopathologically in AD plausibly leads to degeneration of affected nerve cells. At least one study showed decreases in histamine and histidine levels in frontal, temporal and occipital cortices and in the caudate nucleus of brains from AD patients examined post mortem (Mazurkiewics and Wsonwah, *Can. J. Physiol. Pharmacol.*, 67:75–78 (1989)).

Histamine is a chemical messenger involved in various complex biological actions. It is widely distributed in the plant and animal kingdoms. In mammals, including man, it occurs mainly in an inactive bound form in most body tissues. When released, histamine interacts with specific macromolecular receptors on the cell surface or within a target cell to elicit changes in many different bodily functions. Histamine (4(2-aminoethyl) imidazole) is a base. Its chemical structure is:

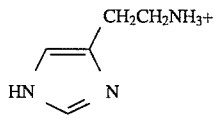

Histamine receptor pharmacology has revealed three subtypes of receptors which mediate (or are associated with) the activity of histamine. These receptors are most commonly referred to as $H_1$, $H_2$, and $H_3$. The most recently discovered of these receptors is the $H_3$ histamine receptor. Early studies suggested the presence of another histamine receptor when it was demonstrated that histamine inhibits its own synthesis and release in brain slices by a negative feedback process operating at the level of histaminergic nerve-endings (see, for example, Arrang, J. M. et al. *Nature* 302:832–837 (1983)). More recently, the $H_3$ receptor has been shown to function as a pre-synaptic autoreceptor inhibiting histamine synthesis and histamine release from neurons, especially in the control nervous system (Arrang, et al. *Nature* 327:117–123 (1987)). The presence of $H_3$ receptors in peripheral tissues has also been reported and here too they appear to be involved with the nervous system. Thus, histamine depresses sympathetic neurotransmission in the guinea pig mesenteric artery by interacting with $H_3$ receptors on the perivascular nerve terminals (Ishikawa and Sperelakis, *Nature* 327:158 (1987)). This important observation suggests that histamine may control the release of other neurotransmitters (Tamura et al., *Neuroscience* 25:171 (1988)). Inhibitory histamine $H_3$ receptors also exist in the guinea pig ileum where their role appears to be to modify the magnitude of histamine contraction, rather than affecting histamine release (Trzeciakowski, *J. Pharmacol. Exp. Therapy* 243:847 (1987)). Particularly intriguing is the discovery of $H_3$ receptors in the lung (Arrang et al. supra (1987)). The presence of histamine $H_3$ receptors in the lung raises the question of whether they control histamine release in anaphylaxis and whether they may be manipulated to provide therapy in asthma. Indeed it has been suggested that $H_3$ receptors may have a modulating role on excitatory neurotransmission in airways. Generally, however, $H_3$ receptor inhibition tends to increase histamine activity, with potentially detrimental effects. Thus, it is desirable to avoid introducing $H_3$ receptor antagonists that act on peripheral tissues.

Histamine $H_3$ receptor activation was found to inhibit acetylcholine release in a guinea pig ileum model (Poli et al., *Agents and Actions* 33: 167–169). Selective $H_3$-receptor blockers reversed the histamine-induced inhibitory effect. Histamine also decreased serotonin release; this effect was reversed with an $H_3$-antagonist, and was suggested to operate via the histamine $H_3$-receptors (Schlicker et al., *Naunyn-Schmiedaberg's Arch. Pharmacal.* 337: 588–590 (1988). Activation of $H_3$-receptors was found to inhibit excitatory presynaptic potentials (Arrang et al., *J. Neurochem.* 51:105 (1988)).

One reported highly specific competitive antagonist of histamine $H_3$ receptors is thioperamide (Arrang et al., supra (1987)). Although thioperamide is a very potent antagonist in vitro ($K_i$=4.3 nmol/L), relatively high doses are required in vivo to inhibit histamine release from the brain in rats (Ganellin et al., *Collect. Czech. Chem. Commun.* 5:2448–2455 (1991)). Ganellin et al. suggests that this most probably results from poor penetration through the blood-brain-barrier by this peramide, although the pharmacokinetic properties of thioperamide may also play a role. Moreover, the thiourea functionality found in thioperamide may result in higher intrinsic toxicity of thioperamide.

Thiourea-containing drugs are known to be associated with undesirable side effects in clinical use. For example, with thiourea-containing drug molecules that are used to treat hyperthyroidism, agranulocytosis is known to be a serious, and occasionally fatal, toxic effect in clinical use (see, e.g., Brimblecombe et al. *Gastroenterology* 74:339–346 (1978)). The thiourea-containing histamine $H_2$-receptor antagonist metiamide caused a low incidence of granulocytopenia in peptic ulcer patients and was withdrawn from clinical use (Forrest et al., *Lancet* 1:392–393 (1975)). In high dose, repeated dose toxicological studies in dogs, incidences of agranulocytosis were seen at 162 mg/kg/day (Brimblecombe et al., "Toxicology of Metiamide, *International Symposium on Histamine $H_2$ - Receptor Antagonists*, Wood and Simpkins, Smith Kline & French, pp. 53–72 (1973)). A proportion of dogs (<10%) died acutely with pulmonary edema and pleural effusion. The metiamide isostere cimetidine, in which the thiourea group was replaced by an alternative group (cyanoguanidine), did not cause granulocytopenia, or any other side effects in animal toxicity studies or in clinical usage by multimillions of patients, indicating that the toxicological problems with metiamide could be attributed to the presence of the thiourea group (Brimblecomb et al., supra). It is likely that the thiourea functionality, with its association with toxicological phenomena and its likelihood of inducing undesirable side effects, could limit the clinical development of thioperamide.

Although some predictions have been made concerning the ability of molecules to pass through the blood brain barrier, these predictions are at best speculative. The rate and extent of entry of a compound into the brain are generally considered to be determined primarily by partition coefficient, ionization constant(s) and molecular size. No single partition solvent system has emerged as a universally applicable model for brain penetration, although the octanol water system has received particular attention, and Hansch and coworkers have suggested that a partition coefficient in this system of about 100 is optimal for entry into the central nervous system (CNS) (Glave and Hansch, *J. Pharm. Sci.*, 61:589 (1972); Hansch et al., *J. Pharm. Sci.*, 76:663 (1987)). Comparisons between known $H_2$ antagonists, however, suggest that there is no such simple relationship between their brain penetration and octanol water partition coefficients (Young et al., *J. Med. Chem.* 31:656 (1988)). The comparison of the ability of histamine $H_2$ receptor antagonists to cross the blood brain barrier suggests that brain penetration may increase with decreasing over-all hydrogen binding ability of a compound (Young et al., supra). However, optimizing $H_2$ receptor antagonists to improve brain penetration reduced antagonist potency (Young et al., supra). Thus it is fundamentally difficult to optimize both blood brain barrier permeability and function of a compound.

It is therefore an object of the present invention to provide novel potent histamine $H_3$-receptor antagonists that are better able to penetrate the blood-brain-barrier than previously reported compounds.

Further it is an object of the present invention to provide novel potent histamine $H_3$-receptor antagonists that have reduced toxicity compared to other known $H_3$ antagonists.

Another object of the present invention is to provide histamine $H_3$-receptor antagonists that will act selectively on the brain and have limited activity on $H_3$ receptors in peripheral tissues.

It is yet another object of the present invention to provide a novel class of histamine $H_3$-receptor antagonists.

3. SUMMARY OF THE INVENTION

The present invention provides novel compounds having activity as histamine $H_3$-receptor antagonists. In a preferred aspect, the compounds of the invention exhibit ready penetration of the blood-brain-barrier and reduced toxicity. The novel compounds of this invention include compounds of the formula:

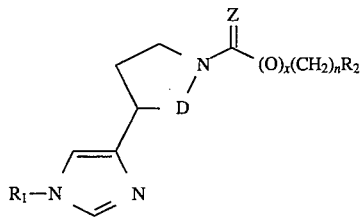

I wherein D is $CH_2$ or $CH_2$—$CH_2$, Z represents S or O, preferably O, x is 0 or 1, n is an integer from 0 to 6, $R_1$ represents preferably hydrogen, or a hydrolyzable group, but can be a lower alkyl or aryl group, and $R_2$ represents a linear chain, branched chain or carbocyclic group or aryl group of up to about 20 carbon atoms, and salts thereof. If $R_2$ is tert-butyl, cyclohexyl, or dicyclohexylmethyl, x or n must not be 0. If $R_2$ is adamantane, the sum of x and n must be greater than 1. The various alkyl or aryl groups can have functional group substituents.

It has been discovered that amide or carbamate functional groups can be used to join alkyl or aryl substituents to the piperidyl nitrogen of 4(4-piperidyl)-1H-imidazole groups. Other cyclic imides, particularly pyrrolidyl or cycloheptamidyl ($C_6H_{11}N$) can be substituted for piperidine. In a preferred aspect, the compounds of the invention are surprisingly effective at transport across the blood brain barrier, thus limiting their effects primarily to cerebral histamine $H_3$-receptors, and are also less toxic than histamine $H_3$-receptor antagonists based on a thiourea functional group.

In addition, the present invention encompasses a pharmaceutical composition comprising a compound of the invention, and a method of using a compound or pharmaceutical composition of the inspection in an animal, particularly in a human, to treat Alzheimer's disease and other dementias by ameliorating the cognitive defects and neurodegenerative effects associated therewith. The histamine $H_3$-receptor antagonists of the invention have additional therapeutic uses where increased arousal and attention is desired.

Furthermore, the present invention encompasses a method of suppressing appetite in an animal, particularly a human, comprising administering to the animal an effective amount of a compound of the present invention. Thus, the invention encompasses the treatment of obesity in animals suffering from such a disorder. The invention further encompasses a pharmaceutical composition comprising a compound of the present invention; and optionally a pharmaceutically acceptable carrier. This pharmaceutical composition can be administered to suppress appetite in an animal, particularly a human.

4. BRIEF DESCRIPTION OF THE FIGURES

FIG. 1. Binding of $N^\alpha$-methylhistamine to rat cortical homogenate. Open box: total bound; x'ed box: specific binding; closed box: non-specific binding.

Figure 2:
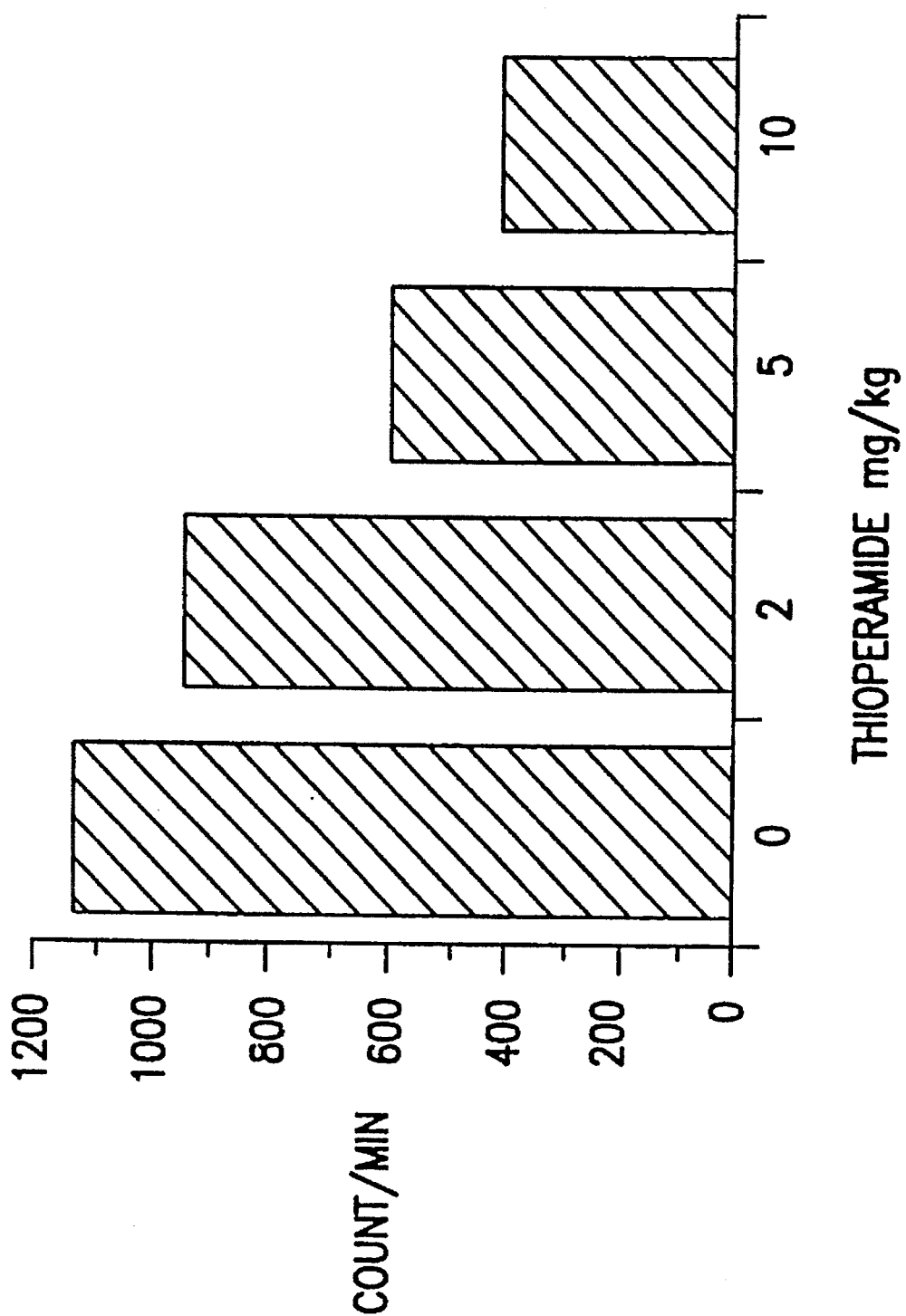

FIG. 2. Binding of $^3$H-labeled $N^\alpha$-methylhistamine to the cortical homogenate of thioperamide injected rats.

Figure 3:
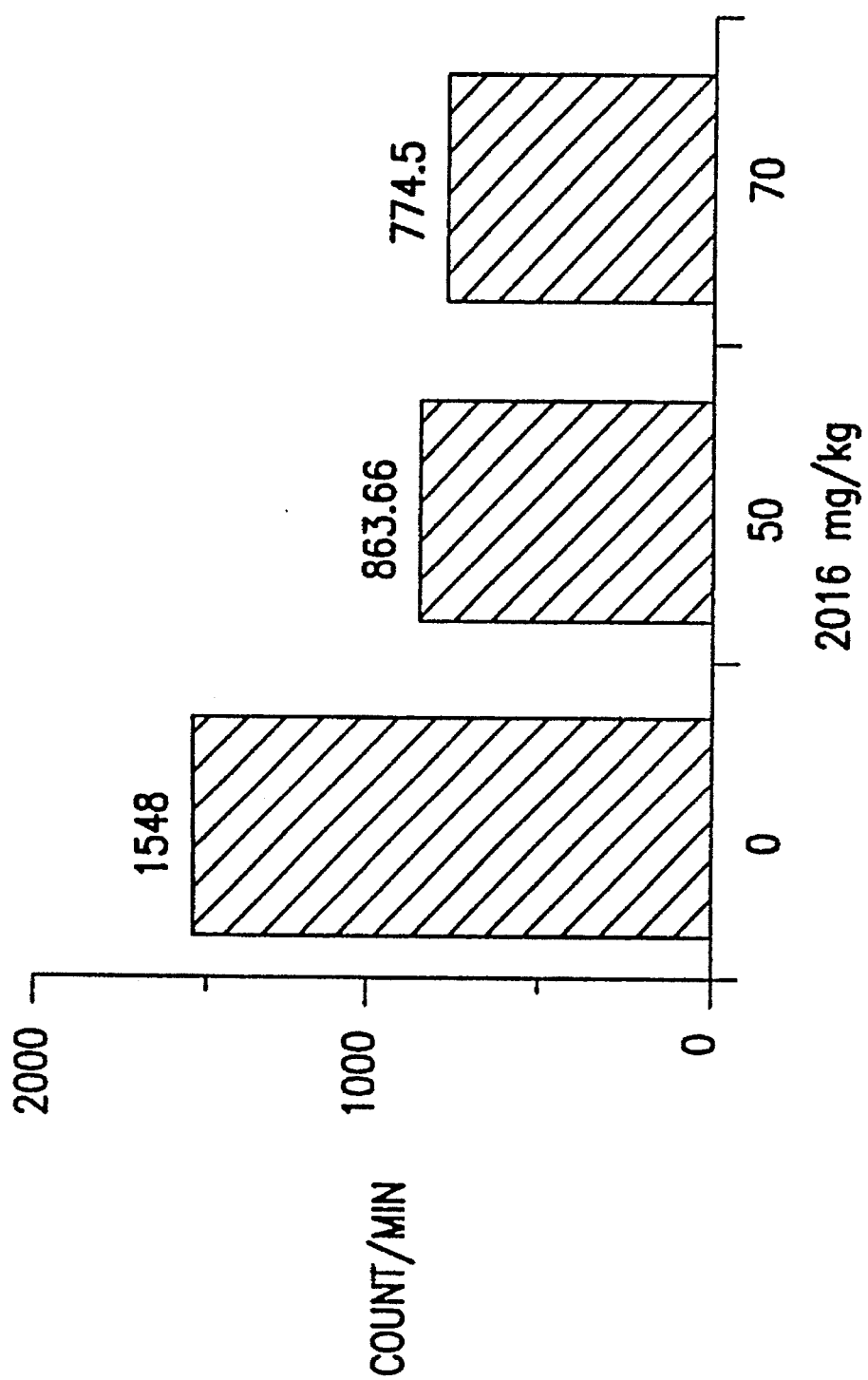

FIG. 3. Binding of $^3$H-labeled $N^\alpha$-methylhistamine to the cortical homogenate of compound 1 injected rats.

Figure 4:
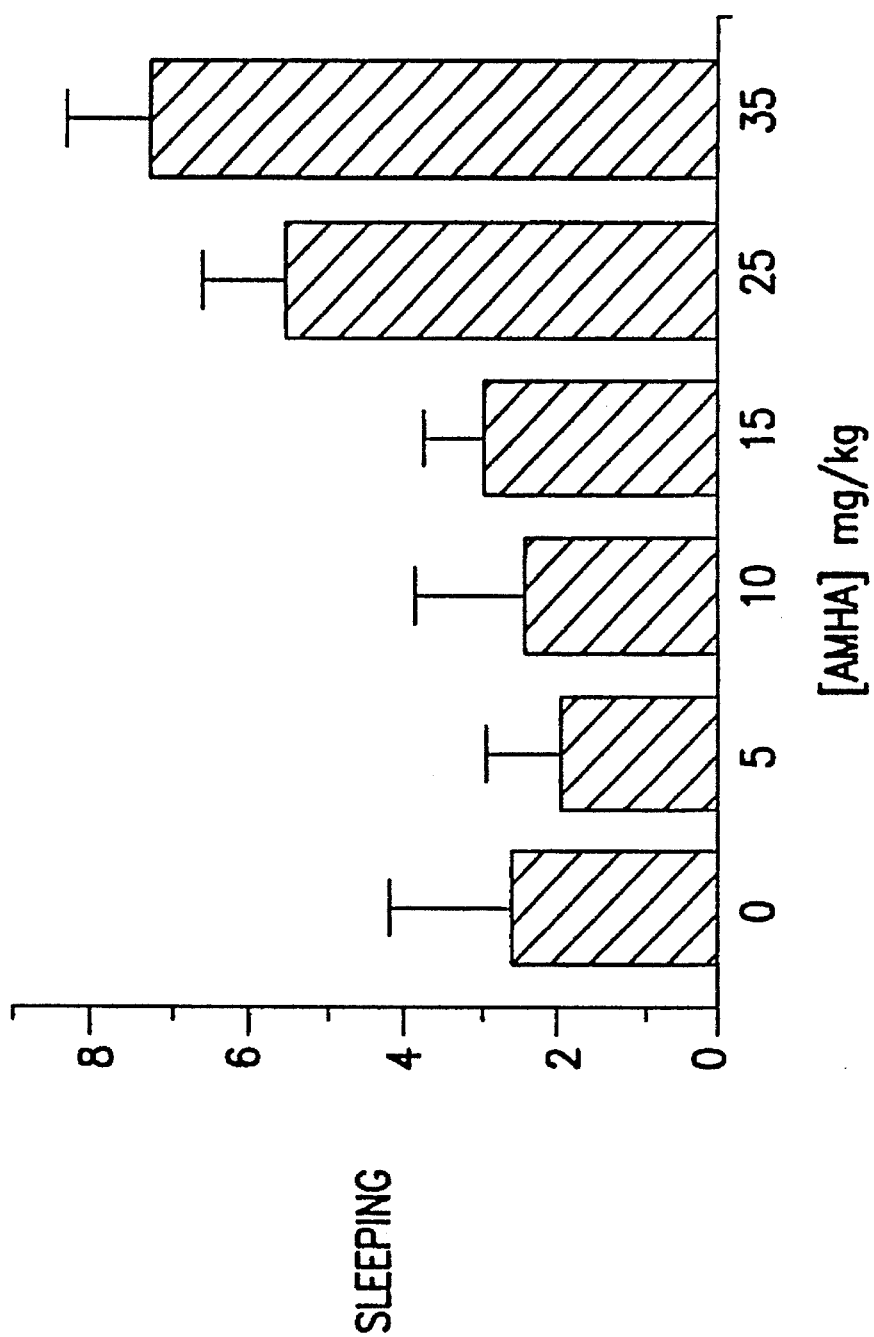

FIG. 4. The effect of α-methylhistamine on sleeping one hour after injection.

Figure 5:
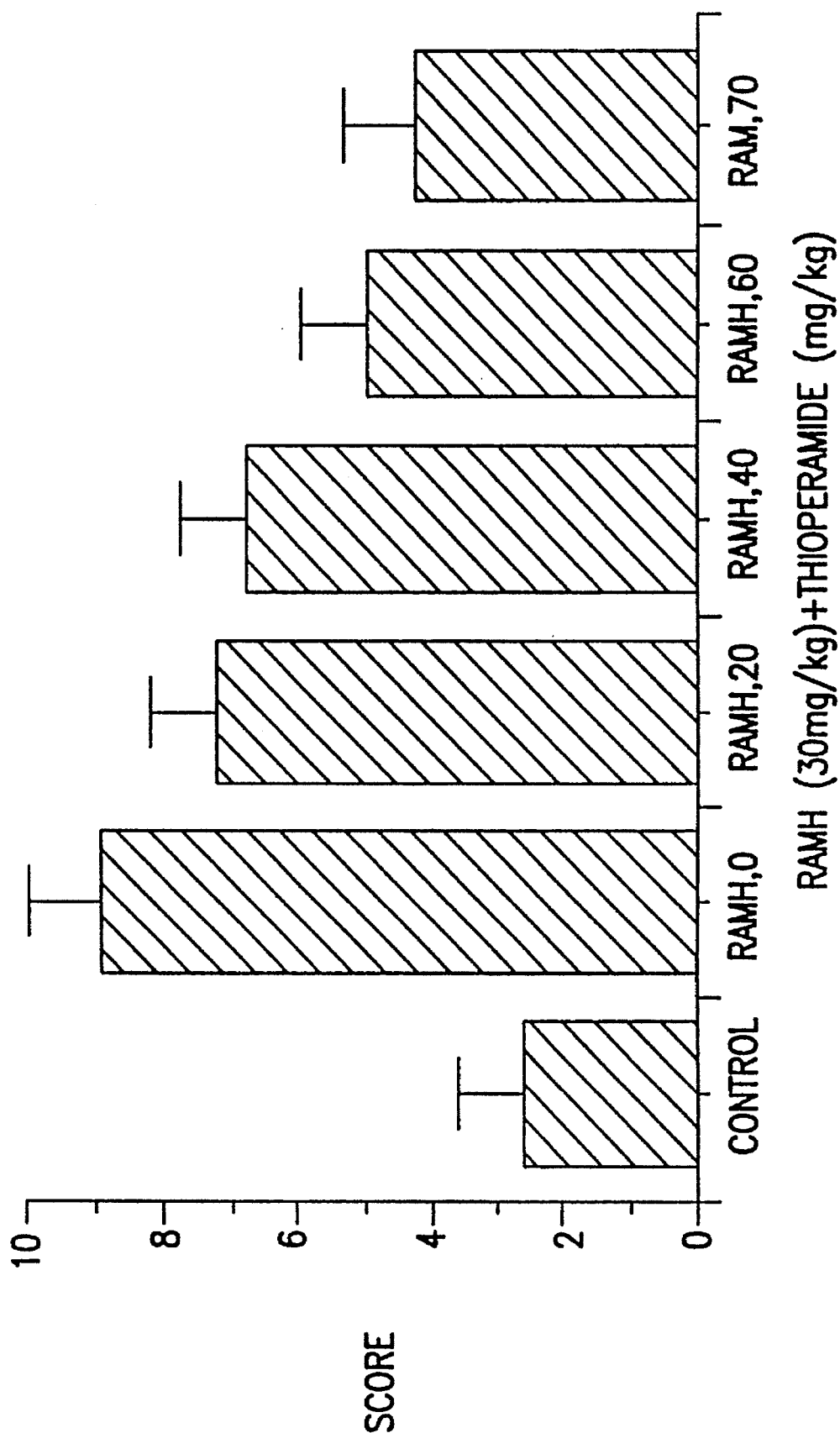

FIG. 5. The effect (dose-response) of thioperamide on sleep induced by R(-)-α-methylhistamine (30 mg/kg).

Figure 6:
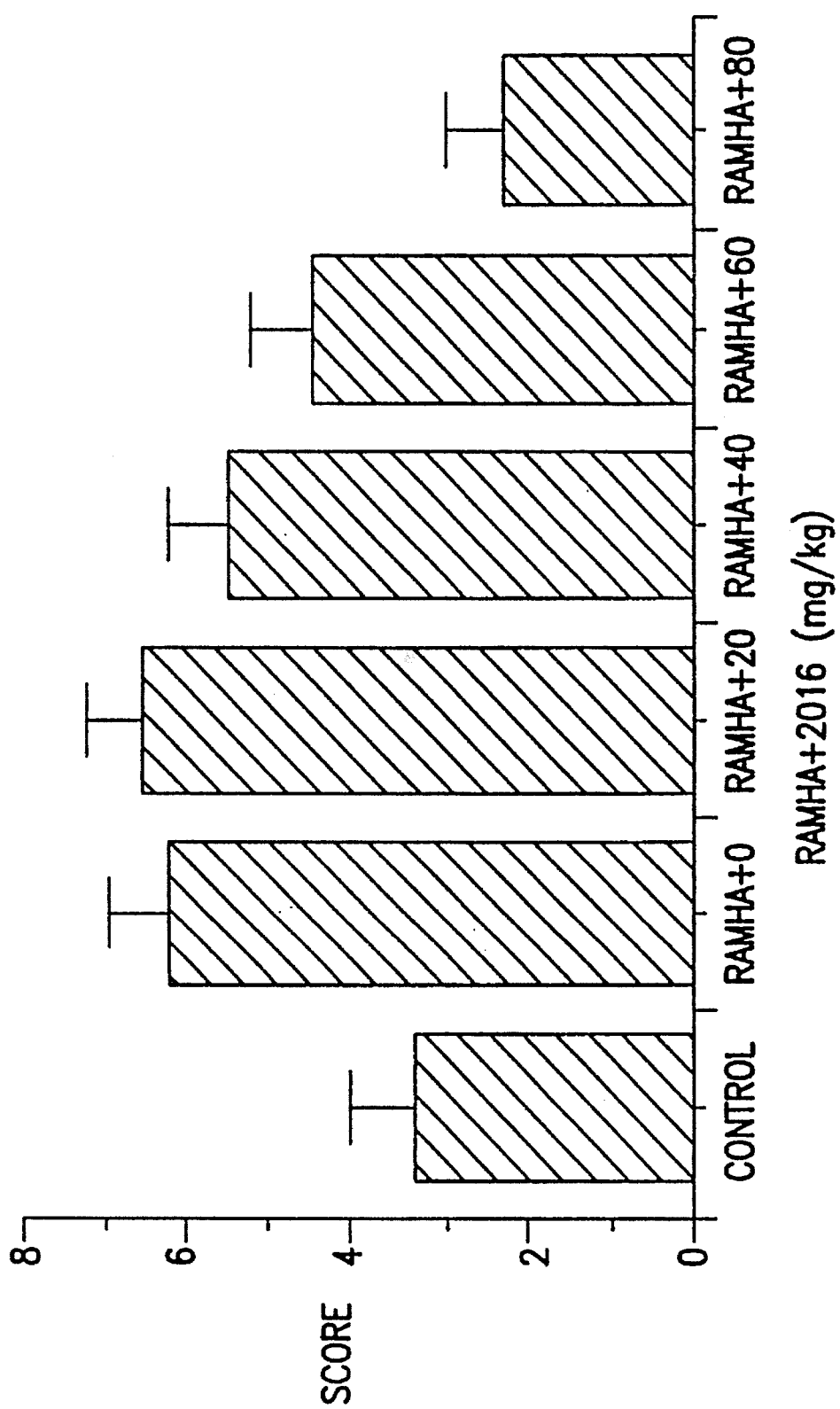

FIG. 6. The effect (dose-response) of compound 1 on sleep induced by R(-)-α-methylhistamine (25 mg/kg).

Figure 7:
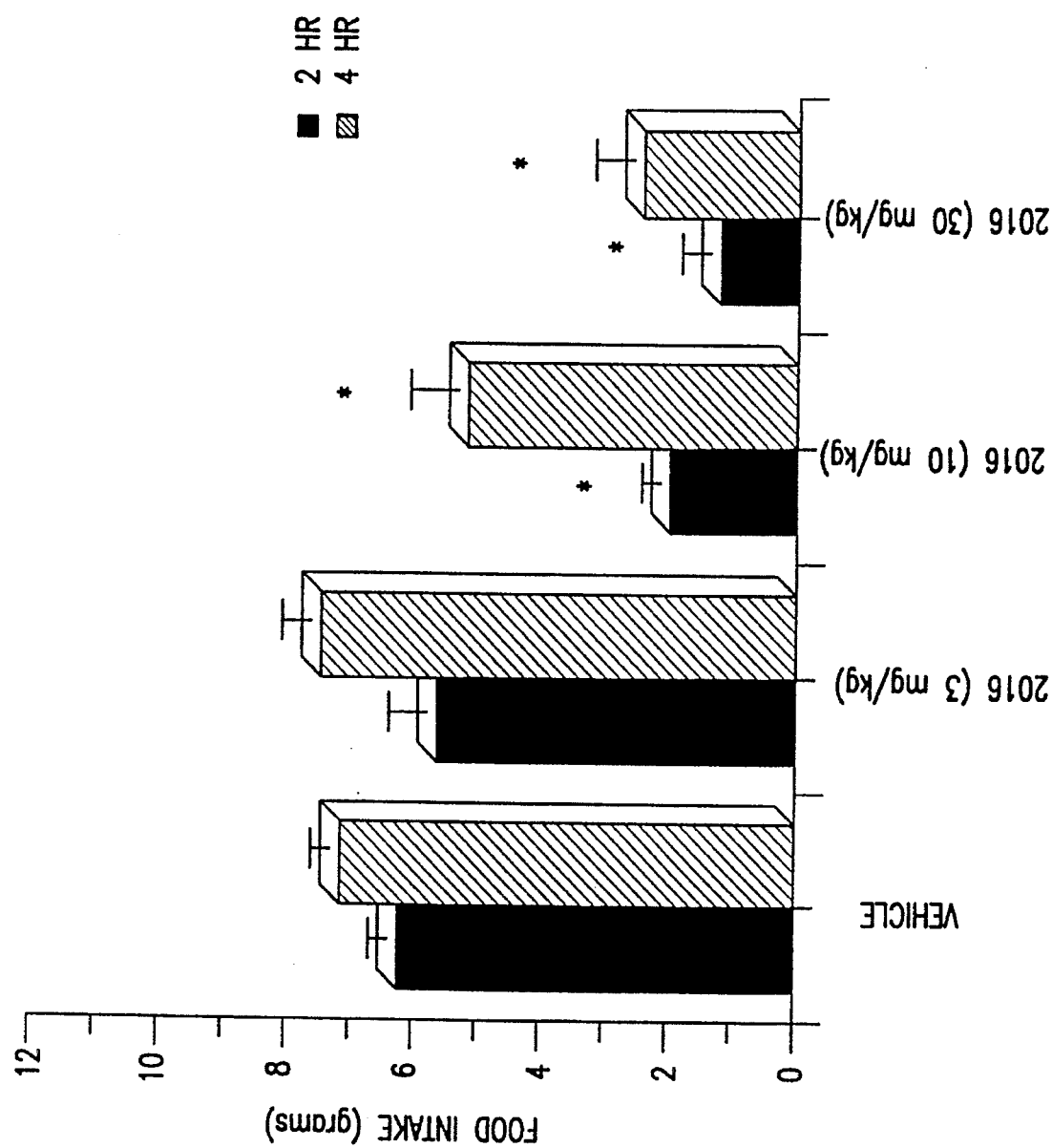

FIG. 7. The effect of compound 1 on 2 and 4 hour food intake in 24-hour-fasted rats. Solid bar: 2 hour food intake. Cross-hatched bar: 4 hour food intake.

Figure 8:
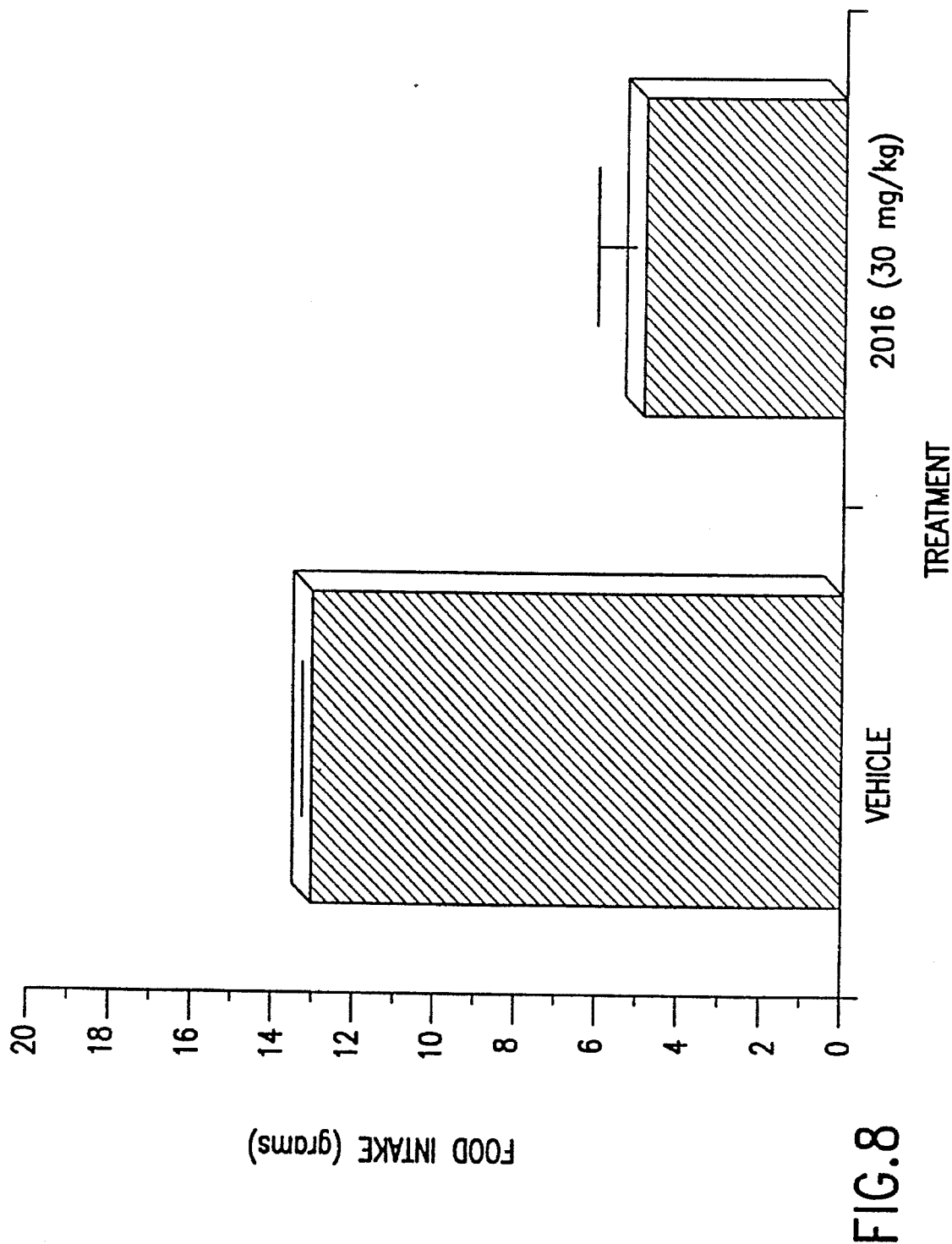

FIG. 8. The effect of compound 1 on 6 hour food intake in 24-hour-fasted rats.

5. DETAILED DESCRIPTION OF THE INVENTION

The compounds of the present invention are compounds of the general formula.

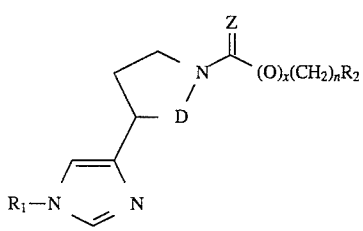

wherein D is $CH_2$ or $CH_2$—$CH_2$, Z represents sulfur (S) or oxygen (O), preferably O, x is 0 or 1, n is an integer from 0 to 6, $R_1$ represents hydrogen, an in vivo hydrolyzable group, a lower alkyl group, a lower cyclic alkyl group, or a lower aryl group, and $R_2$ represents a substituted or unsubstituted linear chain or branched chain alkyl group of up to about 20 carbon atoms, a substituted or unsubstituted carbocyclic group of up to about 20 carbon atoms including mono and bicylic moieties, and a substituted or an unsubstituted aryl group of up to about 20 carbon atoms, or any combination of above-mentioned groups, or salts thereof. In a specific embodiment, $R_2$ can represent a disubstituted methyl, such as but not limited to dicyclohexyl methyl (—$CH(C_6H_{11})_2$), diphenyl methyl (—$CH(C_6H_5)_2$), and the like. If $R_2$ is tert-butyl, cyclohexyl, or dicyclohexylmethyl, x or n must not be 0. If $R_2$ is adamantane, the sum of x and n must be greater than 1.

In a preferred embodiment, $R_1$ is hydrogen. It is also contemplated that $R_1$ can be a hydrolyzable leaving group, such as an acyl or carbamyl, including where $R_1$=—$CZ(O)_x(CH_2)_nR_2$, as in I above. It is well known that N-acylimidazoles are hydrolytically labile, and $R_1$ may be selected such that it yields the parent imidazole compound in vivo at an optimal rate. Such hydrolysis will yield the compound with hydrogen as $R_1$. Thus, the contemplated compounds of the invention with a hydrolyzable substituent at $R_1$ are functionally equivalent to the preferred embodiment, i.e., where $R_1$ is hydrogen. $R_1$ can also be a lower linear chain, branched chain, or cyclic alkyl, or a lower aryl. The term "lower" as applied to the alkyl or aryl substituents at $R_1$ indicates the presence of up to seven carbon atoms. In specific embodiments infra, $R_1$ is methyl, benzyl, methylcyclohexane, N-cyclohexylformamide, benzaldehyde, and t-butylaldehyde.

In yet a further embodiment, the nitrogen atom at position 3 of the imidazole ring can be substituted with a lower alkyl or aryl group, or with a hydrolyzable leaving group.

In a preferred embodiment, D is $CH_2$—$CH_2$, resulting in a piperidine ring structure. However, it is contemplated that D can be $CH_2$, yielding a pyrrolidine ring structure. In yet another embodiment, D can be $(CH_2)_3$, yielding a cycloheptimide (seven membered heterocycle with one nitrogen). While orientation of the imidazole group distal to the N of the piperidine is preferred, the invention contemplates the imidazole at the 2 or 3 position on the piperidine (or the 2 position of pyrrolidine, or the 2 and 3 position of the cycloheptimide ring). These alternate embodiments can be used instead of the piperidyl embodiment with the imidazole group located at the 4 position, although the piperidyl embodiment is preferred.

Although the present invention is not limited to any mechanistic theory, it is believed that the blood brain barrier is permeable to the compounds of the present invention in part because of the subtle decrease in polarity afforded by an amide or carbamate bond linking the (-(O)$_x$(CH$_2$)$_n$R) moiety (e.g., a hydrophobic tail) to the 4(4-piperidyl)-1H-imidazole (or 4(3-pyrrolidyl)-1H-imidazole) structure. With slightly less polarity and hydrogen-bonding capability than urea or thiourea, the amide or carbamate functionality can more efficiently traverse the blood brain barrier. Moreover, the dipole of the amide or carbamate is distal to the hydrophobic tail, more proximal to the imidazole (which is a fairly polar group), and thus tends to effect greater amphiphilicty in the molecule. That the compounds of the invention retain amphiphilic character is important for solubility in aqueous solution. Solubility in aqueous solution is desirable for a compound to be used therapeutically in an animal particularly in a human. That such a subtle difference, use of an amide or carbamate functionality, should perceptibly alter blood brain barrier permeability may be considered to be surprising since it is not generally appreciated.

In preferred embodiments, a bulky hydrocarbon $R_2$ group is chosen so that the net hydrophilicity of the $H_3$-receptor antagonist is increased, and the steric effects of a bulky substituent at $R_2$ are decreased, by increasing the number of methylenes in a straight chain alkyl group (i.e., in Formula I, n>1). In a specific embodiment, a tetramethylene bound to the amide or carbamate group is used. Preferably a cyclic alkyl or aryl group is linked to the amide or carbamate via the straight chain alkyl group. In a specific embodiment, tetramethylene cyclohexane (cyclohexylbutyl) is bound to an amide. Although specific hydrophobic alkyl and aryl groups have been mentioned, one of ordinary skill in the art will recognize that there are many possible hydrophobic groups for use in the compounds of the invention. These fall within the scope of the instant invention.

Thus, $R_2$ can be one or more bulky substituent groups. As stated above, in a preferred aspect of the invention, the bulky substituents are removed from the amide or carbanate group on the piperidyl-imidazole by increasing n. In one embodiment, $R_2$ is $CHR_3R_4$, in which n is 3 or 4 and $R_3$ and $R_4$ are cyclohexyl, phenyl, or the like. $R_3$ and $R_4$ can be the same group or different groups. In another embodiment, $R_2$ is decalin or adamantane or the like. If $R_2$ is adamantane, preferably n is greater than 1, but the sum of x and n must be greater than 1.

As used herein, the phrase linear chain or branched chained alkyl groups of up to about 20 carbon atoms means any substituted or unsubstituted acyclic carbon-containing compounds, including alkanes, alkenes and alkynes. Examples of alkyl groups include lower alkyl, for example, methyl, ethyl, n-propyl, iso-propyl, n-butyl, iso-butyl or tert-butyl; upper alkyl, for example, octyl, nonyl, decyl, and the like; and lower alkylene, for example, ethylene, propylene, propyldiene, butylene, butyldiene, and the like. The ordinary skilled artisan is familiar with numerous linear and branched alkyl groups, which are with the scope of the present invention.

In addition, such alkyl group may also contain various substituents in which one or more hydrogen atoms has been replaced by a functional group. Functional groups include but are not limited to hydroxyl, amino, carboxyl, amide, esther, ether, and halogen (fluorine, chlorine, bromine and iodine), to mention but a few.

As used herein, substituted and unsubstituted carbocyclic groups of up to about 20 carbon atoms means cyclic carbon-containing compounds, including but not limited to cyclopentyl, cyclohexyl, cycloheptyl, admantyl, and the like. Such cyclic groups may also contain various substituents in which one or more hydrogen atoms has been replaced by a functional group. Such functional groups include those described above, and lower alkyl groups as described above. The cyclic groups of the invention may further comprise a heteroatom. For example, in a specific embodiment, $R_2$ is cyclohexanol.

As used herein, substituted and unsubstituted aryl groups means a hydrocarbon ring bearing a system of conjugated double bonds, usually comprising six or more even number of π (pi) electrons. Examples of aryl groups include, but are not limited to, phenyl, naphthyl, anisyl, toluyl, xylenyl and the like. According to the present invention, aryl also includes heteroaryl groups, e.g., pyrimidine or thiophene. These aryl groups may also be substituted with any number of a variety of functional groups. In addition to the functional groups described above in connection with substituted alkyl groups and carbocyclic groups, functional groups on the aryl groups can be nitro groups.

As mentioned above, $R_2$ can also represent any combination of alkyl, carbocyclic or aryl groups, for example, 1-cyclohexylpropyl, benzyl cyclohexylmethyl, 2-cyclohexylpropyl, 2,2-methylcyclohexylpropyl, 2,2-methylphenylpropyl, 2,2-methylphenylbutyl.

In a specific embodiment, $R_2$ represents cyclohexane, and n=4 (cyclohexylvaleroyl). In another specific embodiment, $R_2$ represents cinnamoyl.

Particularly preferred are compounds of the formula:

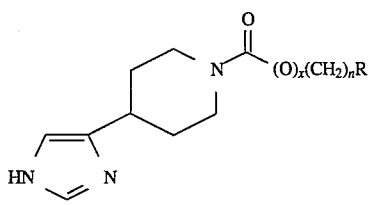

wherein x is 0 or 1, n is an integer from 0 to 6, more preferably n=3–6, and most preferably n=4, and R is as defined for $R_2$ above. Examples of preferred alkyl groups for R include but are not limited to cyclopentyl, cyclohexyl, admantane methylene, dicyclohexyl methyl, decanyl and t-butyryl and the like. Examples of preferred aryl and substituted aryl groups include but are not limited to phenyl, aryl cyclohexyl methyl and the like.

5.1. SYNTHESIS OF THE COMPOUNDS

The compounds of the present invention can be synthesized by many routes. It is well known in the art of organic synthesis that many different synthetic protocols can be used to prepare a given compound. Different routes can involve more or less expensive reagents, easier or more difficult separation or purification procedures, straightforward or cumbersome scale-up, and higher or lower yield. The skilled synthetic organic chemist knows well how to balance the competing characteristics of synthetic strategies. Thus the compounds of the present invention are not limited by the choice of synthetic strategy, and any synthetic strategy that yields the compounds described above can be used.

As shown in the Examples, infra, two general procedures can be used to prepare the instant compounds. Both involve condensation of an activated (electrophilic) carbonyl with the nucleophilic piperidyl nitrogen of 4-(4-piperidyl)-1H-imidazole.

The first procedure involves preparing the acid chloride derivative or acid anhydride of a carbonyl, i.e., activating the carbonyl. This activated carbonyl is added in molar excess to the piperidyl-imidazole in the presence of a molar excess of an unreactive base, for example, but not limited to, dicyclohexyl amine.

The second procedure is to condense the piperidyl-imidazole with a slight molar excess of a dicarbonate, again in the presence of an unreactive base, for example and not by way of limitation, triethylamine. This method can be used especially in the preparation of carbamate compounds.

A preferred synthesis of the 4-(4-piperidyl)-1H-imidazole is also provided. Commercially available 4-acetyl pyridine (Aldrich Chemical Co.) is converted into the key intermediate 4-(4-pyridyl)-1H-imidazole by bromination with hydrogen bromide in acetic acid (Barlin, et al., *Aust. J. Chem.* 42:735 (1989)) to yield the bromoacetyl pyridine in high yield. Reaction of bromoacetyl pyridine with formamide at 110° C. affords the substituted imidazole in high yield. The reaction is usually performed without the addition of any solvent. The pyridyl moiety is reduced by catalytic hydrogenation using 5–10% Rhodium on carbon in acidified water at a pressure of 20–55 atmospheres to yield 4-(4-piperidyl)-1H-imidazole. This synthesis is disclosed more fully in copending U.S. patent application Ser. No. 07/862,658, filed by the instant inventors on Apr. 1, 1992, entitled "PROCESS FOR THE PREPARATION OF INTERMEDIATES USEFUL FOR THE SYNTHESIS OF HISTAMINE RECEPTOR ANTAGONISTS," which is specifically incorporated herein by reference in its entirety.

Solvents for use in the synthesis of the compounds of the invention are well known in the art. The solvent must be non-reactive, and the starting materials and base must be soluble in the solvent. Preferably, an aprotic organic solvent of medium to high polarity is used. For example, acetonitrile, can be used. Under appropriate conditions, in the synthesis of carbamates of the invention, an alcohol, e.g., methanol, can be used.

The electrophilic carbonyl group, which contains the $R_2$ moiety, can be obtained from commercial sources, or it may be prepared synthetically. In specific examples, infra, the carbonyl is obtained commercially. Activation of carbonyls is well known. The acid chloride can be prepared by reacting the carboxylic acid with sulfonyl chloride. Alternatively, the acid chloride may be available commercially. In specific embodiments, infra, acid chlorides were obtained from commercial sources (Aldrich Chemical). Similarly, the acid anhydride can be prepared conveniently by reaction of a salt of the carboxylic acid with the acid chloride. In a specific embodiment, the carboxylic acid is reacted with a carbonate acid chloride to form an asymmetric acid anhydride. In another embodiment, the acid anhydride can be obtained commercially. In a specific embodiment, infra, the acid anhydride was obtained from Aldrich Chemical. Dicarbonates for use in the invention are available commercially, e.g., from Aldrich Chemical.

5.2. BIOLOGICAL ACTIVITY

The compounds of the present invention are biologically active in assays for histamine $H_3$-receptor antagonist activity, as well as in a radioligand binding assay in rat brain membranes (e.g., Table I, infra). The binding assay procedure used and its standardization with known $H_3$-receptor antagonists is shown in the examples infra.

Further biological studies can demonstrate that the histamine $H_3$-receptor antagonists of this invention reverse the soporific effects of the histamine $H_3$-receptor agonist, R(-)-alphamethylhistamine in mice when both drugs are administered peripherally (infra). In a specific embodiment, the compound designated No. 2016 reverses the soporific effect of R(-)-alphamethylhistamine.

The data in the Examples, infra, support the view that antagonists of histamine $H_3$-receptors of the invention are useful regulators of the sleep-wakefulness cycle with potentially useful cognitive and behavioral effects in mammals including humans.

In vivo studies can be used to show effectiveness of a compound of the invention to cross the blood-brain barrier, as shown in the examples, infra. The data support the view that drugs of the present invention penetrate the blood brain barrier and are able to exert beneficial central actions in mammals when these drugs are administered to the peripheral circulation.

5.3. THERAPY

The histamine $H_3$-receptor antagonists of the invention can be provided therapeutically for the treatment of a subject suffering from a cognitive disorder or an attention or arousal deficit, according to the present invention. One of ordinary skill in the art would readily determine a therapeutically effective dose of an $H_3$ receptor antagonist of the invention based on routine pharmacological testing and standard dosage testing. In one aspect of the present invention, the compounds can be administered in doses of about 0.01 to about 200 mg/kg, more preferably 1 to 100 mg/kg, and even more preferably 30 to 100 mg/kg. In a specific embodiment, greater than about 20 mg/kg of a compound of the invention was effective to reduce the soporific effect of (R)α-methylhistamine. Included in the routine pharmacological testing are toxicity studies to determine an upper limit dose. Such toxicity studies can include $LD_{50}$ studies in mice, and 15 day toxicity studies in mammals.

The histamine $H_3$-receptor antagonists of the invention are believed to increase the release of cerebral histamine, acetylcholine and serotonin. These compounds can lead to increased arousal and attention. They can also be of benefit in the treatment of cognitive disorders.

Therapy with a compound of the invention is indicated to treat dementia, as either a primary or an adjunct therapy. The compounds of the invention have clinical utility in the treatment of dementia disorders in general. In a preferred embodiment, a compound of the invention can be used in the treatment for Alzheimer's disease. The compounds can also be used to treat presenile and senile dementia, Huntington's chorea, tardive dyskinesia, hyperkinesia, mania, Tourette syndrome and Parkinson's disease, to name but a few. Other specific indications include the treatment of narcolepsy and hyperactivity in children. In another embodiment, the compounds of the invention can be used in the treatment of certain psychoses, for example forms of depression or schizophrenia.

The compounds of the invention can be used to arouse victims of comas induced by stroke, drugs or alcohol. In another embodiment, the compounds of the invention can be used to increase wakefulness, where this effect is desired. For example, the compounds of the invention, which are preferentially targeted to $H_3$ receptors in the brain, can be used to counteract the soporific effect of some antihistamines without negating the therapeutic effects of the antihistamines on peripheral tissue, e.g., lung. Thus allergy patients can relieve some of the side effects of antihistamine therapy. Similarly, the compounds of the invention can be used to reverse overdose of barbiturates and other drugs.

5.3.1. Appetite Suppression

The histamine $H_3$-receptor antagonists of the present invention have been found to be useful in animals, particularly humans, as appetite suppressants. Thus, in another embodiment of the present invention, these compounds are used to control weight gain, to treat obesity and to promote weight loss, as well as any other condition wherein appetite suppression is desirable.

The present invention provides a method of suppressing appetite in an animal, including but not limited to a human, which comprises administering to the animal, an effective amount of a compound of the present invention.

In specific embodiments, the present invention encompasses a method of suppressing appetite in an animal, including but not limited to a human, which comprises administering to an animal, including a human, an effective amount of a compound of formula I or formula II, or a pharmaceutically acceptable salt thereof.

In a most preferred embodiment, the present invention encompasses a method for suppressing appetite in an animal, including but not limited to a human, which comprises administering to an animal, including a human, an effective amount of 4-(1-cyclohexylvaleroyl-4-piperidyl)-1H-imidazole (compound 1) or a pharmaceutically acceptable salt thereof.

The invention also provides pharmaceutical compositions useful as appetite suppressants which comprise an effective amount of a compound of the present invention or a pharmaceutically acceptable salt thereof; and optionally a pharmaceutically acceptable carrier or excipient. In particular, the present invention encompasses a pharmaceutical composition comprising an effective amount of 4-(1-cyclohexylvaleroyl-4-piperidyl)-1H-imidazole (compound 1) or a pharmaceutically acceptable salt thereof; and optionally a pharmaceutically acceptable carrier or excipient.

An effective amount is an amount sufficient to achieve appetite suppression. One of ordinary skill in the art can readily determine an effective amount of a compound of the present invention based on routine pharmacological testing and standard dosage testing. In one embodiment of the present invention, an effective amount of the compounds disclosed here is about 0.01 to about 200 mg/kg, more preferably 0.1 to 100 mg/kg, and even more preferably 30 to 100 mg/kg. The doses of the present invention can be given in divided or multiple doses over time as needed by the particular subject.

It is noted that the terms "appetite suppression" or "suppressing appetite" are known to those skilled in the art and these are used herein consistently therewith. These terms as used herein include a reduction, decrease or amelioration in appetite, a reduction, decrease or amelioration in the desire or craving for food, a reduction, decrease or amelioration in food intake. Appetite suppression can result in weight loss or weight control as desired. In a specific embodiment, the appetite suppressant of the present invention can be used to treat obesity and any related condition in which weight control is desired, including but not limited to severe and moderate obesity as well as overweight subjects.

5.4. PHARMACEUTICAL COMPOSITIONS AND METHODS OF ADMINISTRATION

The effective dose of a compound of the invention, and the appropriate treatment regime can vary with the indication and patient condition, e.g., the treatment of a dementia or the treatment of tiredness may require different doses and regimens. These parameters are readily addressed by one of ordinary skill in the art and can be determined by routine experimentation.

A therapeutic compound of the invention may also contain an appropriate pharmaceutically acceptable carrier or excipient, diluent or adjuvant, i.e., the compound can be prepared as a pharmaceutical composition. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, magnesium carbonate, magnesium stearate, sodium stearate, glycerol monostearate, talc, sodium chloride, dried skim milk, glycerol, propylene, glycol, water, ethanol and the like. These compositions can take the form of solutions, suspensions, tablets, pills, capsules, powders, sustained-release formulations and the like. When administering the compounds of the present invention as an appetite suppressant, the preferred dosage form is orally by tablet, pill or capsule. Suitable pharmaceutical carriers are described in "Remington's Pharmaceutical Sciences" by E. W. Martin. Such compositions will contain an effective therapeutic amount of the active compound together with a suitable amount of carrier so as to provide the form for proper administration to the patient. While intravenous injection is a very effective form of administration, other modes can be employed, including but not limited to intraventricular, intramuscular, intraperitoneal, intra-arteriolar, and subcutaneous injection, and oral, transdermal, nasal and parenteral administration.

The therapeutic agents of the instant invention may be used for the treatment of animals, and more preferably, mammals, including humans, as well as mammals such as dogs, cats, horses, cows, pigs, guinea pigs, mice and rats.

In another embodiment, the therapeutic compound can be delivered in a vesicle, in particular a liposome (see Langer, Science 249:1527–1533 (1990); Treat et al., in Liposomes in the Therapy of Infectious Disease and Cancer, Lopez-Berestein and Fidler (eds.), Liss, New York, pp. 353–365 (1989); Lopez-Berestein, ibid., pp. 317–327; see generally ibid.)

In yet another embodiment, the therapeutic compound can be delivered in a controlled release system. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989)). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J. Macromol. Sci. Rev. Macromol. Chem. 23:61 (1983); see also Levy et al., Science 228:190 (1985); During et al., Ann. Neurol. 25:351 (1989); Howard et al., J. Neurosurg. 71:105 (1989)). In yet another embodiment, a controlled release system can be placed in proximity of the therapeutic target, i.e., the brain, thus requiring only a fraction of the systemic dose (see, e.g., Goodson, in Medical Applications of Controlled Release, supra, vol. 2, pp. 115–138 (1984)).

Other controlled release systems are discussed in the review by Langer (Science 249:1527–1533 (1990)).

6. EXAMPLES

A series of compounds were prepared and tested for their histamine $H_3$ receptor antagonist activity. The results are summarized in Table 1. The antagonist activity of the compounds was detected by observing inhibition of $(^3H)$-N-(alpha)methylhistamine activity on rat brain membranes.

6.1. SYNTHESIS OF THE COMPOUNDS

The amide and carbamate compounds of Table 1 were synthesized from 4-(4-piperidyl)-1H-imidazole by three general procedures:

Procedure A: 4-(4-piperidyl)-1H-imidazole and the appropriate acid chloride were conjugated using dicyclohexylamine as base according to the following scheme:

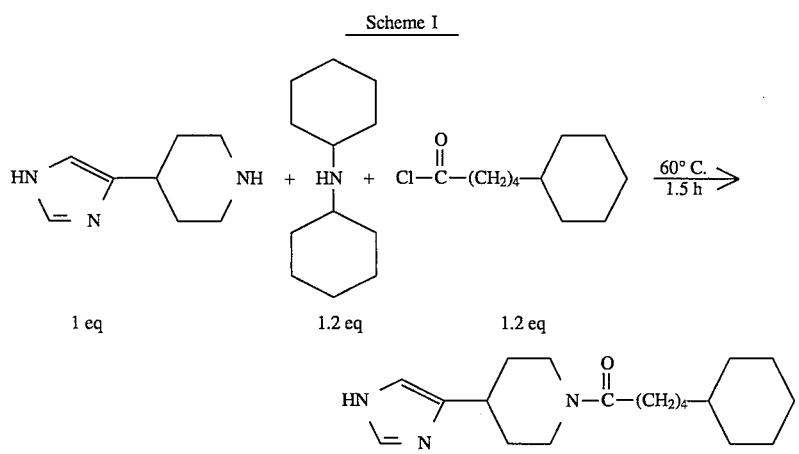

Procedure B: 4-(4-piperidyl)-1H-imidazole and the corresponding acid anhydride were conjugated using triethylamine as base according to the following scheme:

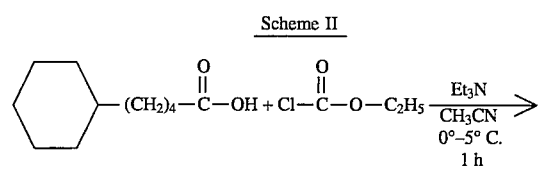

13

-continued
Scheme II

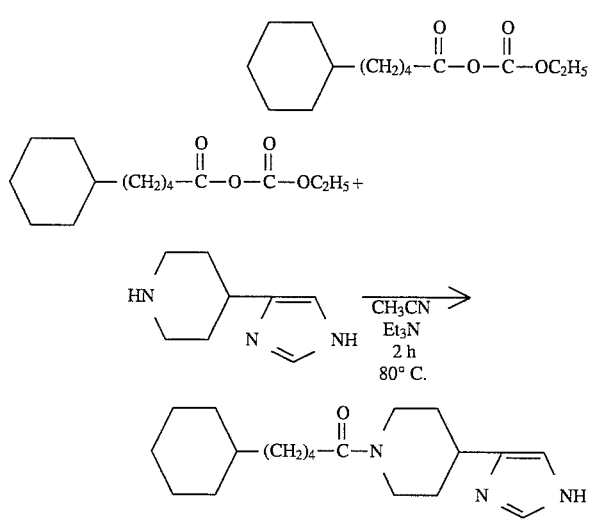

Procedure C: 4-(4-piperidyl)-1H-imidazole and the corresponding dicarbonate were conjugated using triethyl amine as a base according to the following scheme:

6.1.1. PREPARATION OF 4-(1-CYCLOHEXYLVALEROYL-4-PIPERIDYL) 1H-IMIDAZOLE (COMPOUND 1)

To a mixture of 755 mg (5.00 mmol) 4-(4-piperidyl)1-H-imidazole and 942 mg (5.20 mmol) of Scheme III

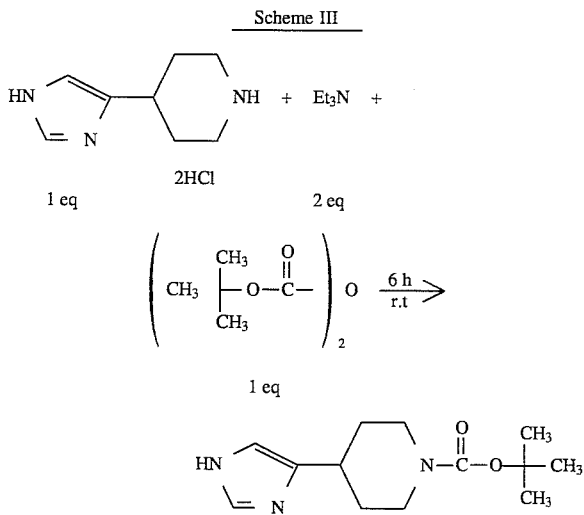

dicyclohexylamine in 10 ml anhydrous acetonitrile at 25° C. was slowly added 1.06 g (5.20 mmol) cyclohexanevaleroyl chloride in 2 ml of dichloromethane over a period of 10 min with stirring; then the reaction mixture was heated at 60° C. for 1.5 h. After cooling to ambient temperature, the solid side product that was obtained (dicyclohexylammonium chloride) was filtered off and the filtrate was concentrated in vacuo to remove acetonitrile. The resulting crude oil was crystallized with methanol: anhydrous diethyl ether to give 1.085 mg of analytically pure product as a yellow powder. Yield: 68%; M.P.: 159° C.; MS: m/e=317 (M+); $^1$H NMR (CDCl$_3$): imidazole H: δ 7.65 (s, 1 H), 6.75 (s, 1 H); cyclohexylbutyl: δ 2.20 (m, 8 H), 1.20 (m, 11 H); piperidyl: 4.65 (d, 2 H), 3.95 (d, 2 H), 3.10 (m, 2 H), 2.84 (m, 1 H), 2.20 (m, 2 H).

14

Compounds No. 3, 4, 5, 6, 7, 8, 9, 10, 11 and 12 in Table I were synthesized in similar manner, i.e., by condensation of the acid chloride with 4(4-piperidyl) 1-H-imidazole in the presence of dicyclohexylcarbodiimide. Purified product was obtained by preparative TLC Silica Gel GF. 60 (2000 Microns) and the solvent of recrystallization was methanol:anhydrous ether (20:80).

Compound No. 3, yield: 70%; oil; MS m/e 275 (M+); $^1$H NMR (CDCl$_3$): imidazole H: δ 7.60 and 6.75 (s, 1 H); piperidine H: complex, δ 4.65 (d, 2 H), 3.90 (d, 2 H), 3.10 (m, 3 H), 2.10 (m, 2 H); cyclohexyl acetyl H: δ 1.50 (m, 11 H), 2.80 (m, 2 H).

Compound No. 4, yield: 67%; oil; MS: m/e 267 (M+); $^1$H NMR (CDCl$_3$): imidazole H: δ 7.50 and 6.60 (s, 1 H); piperidine H: complex, δ 3.90 (d, 2 H), 2.80 (m, 3 H), 2.55 (m, 2 H), 1.80 (m, 2 H); phenyl acetyl H: δ 7.10 (m, 5 H), 1.50 (m, 2 H).

Compound No. 5, yield: 71%; oil; MS: m/e 297 (M+); $^1$H NMR (CDCl$_3$): imidazole H: δ 7.80 and 6.70 (s, 1 H); piperidine H: complex, δ 4.60 (d, 2 H), 3.80 (d, 2 H), 3.10 (m, 3 H), 1.80 (d, 2 H); phenyl propyl H: δ 7.20 (m, 5 H), 2,65 (m, 2 H), 235 (m, 2 H), 2.10 (m, 2 H).

Compound No. 6, yield: 74%; oil; MS: m/e 289 (M+); $^1$H NMR (CDCl$_3$): imidazole H: δ 7.70 and 6.80 (s, 1 H); piperidine H: complex, δ 4.60 (d, 2 H), 3.85 (d, 2 H), 3.10 (m, 3 H), 1.90 (m, 2 H); cyclohexyl ethyl H: δ 1.10 (m, 11 H), 2.00 (br, 2 H), 2.20 (m, 2 H).

Compound No. 7, yield: 75%; oil; MS: m/e 283 (M+); $^1$H NMR (CDCl$_3$): imidazole H: δ 7.60 and 6.70 (s, 1 H); piperidine H: complex, δ 4.60 (d, 2 H) , 3.90 (d, 2 H), 3.10 (m, 3 H), 1.80 (m, 2 H); phenyl ethyl H: δ 7.30 (m, 5 H,) 2.10 (br, 2 H), 1.50 (m, 2 H).

Compound No. 8, yield: 69%; M.P.: 151° C.; MS: m/e 327 (M+); $^1$H NMR (CDCl$_3$): imidazole H: δ 7.65 and 6.80 (s, 1 H); piperidine H: complex, δ 4.70 (d, 2 H) , 4.50 (d, 2 H), 3.60 (m, 1 H), 2.80 (m, 2 H), 2.10 (m, 2 H); adamantyl acetyl H: δ 1.80 (m, 12 H) , 3.10 (m, 2 H), 4.05 (m, 1 H).

Compound No. 9, yield: 62%; M.P.: 148° C. (decomposed); MS: m/e 357 (M+); $^1$H NMR (CDCl$_3$): imidazole H: δ 7.60 and 6.85 (s, 1 H); piperidine H: complex, δ 4.50 (d, 2 H), 4.05 (m, 3 H), 3.40 (d, 2 H), 2.10 (m, 2 H); dicyclohexyl acetyl H: δ 1.50 (m, 22 H), 2.50 (m, 1 H).

Compound No. 10, yield: 64%; oil; MS: m/e 281 (M+); $^1$H NMR (CDCl$_3$): imidazole H: δ 7.75 and 6.60 (s, 1 H); piperidine H: complex, δ 4.70 (d, 2 H), 4.20 (m, 3 H), 2.80 (m, 2 H), 2.10 (d, 2 H); phenyl vinyl H: δ 7.40 (m, 5 H), 6.50 (m, 2 H).

Compound No. 11, yield: 62%; oil; MS m/e 351 (M+); $^1$H NMR (CDCl$_3$): imidazole H: δ 7.50 and 6.40 (s, 1 H); piperidine H: complex, δ 4.60 (d, 2 H) 4.10 (m, 3 H), 2.80 (d, 2 H), 1.80 (m, 2 H); phenyl cyclohexyl acetyl H: δ 7.20 (m, 5 H), 1.80 (m, 11 H), 3.70 (m, 1 H).

Compound No. 12, yield: 72%; M.P.: 136° C.; MS:m/e 304 (M+); $^1$H NMR (CDCl$_3$): imidazole H: δ 7.70 and 6.80 (s, 1 H); piperidine H: complex, δ 4.60 (d, 2 H), 4.00 (m, 2 H), 3.60 (m, 3 H), 1.88 (m, 2 H); cyclohexyl propyl H: complex, δ 1.20 (m, 17 H).

6.1.2. ALTERNATIVE METHOD FOR THE PREPARATION OF 4-(1-CYCLOHEXYLVALEROYL-4-PIPERIDYL) 1H-IMIDAZOLE (COMPOUND 1)

Preparation of acid anhydride: Triethylamine (1.01 g, 10.00 mmol) was slowly added to a stirred solution of 1.84 g (10.00 mmol) cyclohexylpentanoic acid in 60 ml acetonitrile at 0° C. After 30 min. of stirring, 1.08 g (10.00 mmol) of ethylchloroformate was added slowly in 5–7 min., so that the temperature remained between 0° C. and 5° C. After 1 h stirring, the solution was used for the preparation of Compound 1.

Preparation of Compound 1: The freshly prepared acid anhydride was poured into a suspension of 1.54 g (10.20 mmol) of 4(4-piperidyl)imidazole and 1.03 g (10.20 mmol) triethylamine in 70 ml acetonitrile. After 1 h of heating at 80° C., the solution was concentrated under reduced pressure, and the oily residue was taken up with 75 ml water and then extracted with 150 ml ethylacetate. The residual oil was obtained, which crystallized on addition of ethylacetate/hexane. Yield: 74%.

This method provides the desired amide in good yield when the piperidylimidazole is added in slight molar excess, e.g., about a 1.01 to 1 molar ratio, to the asymmetric anhydride.

Compounds No. 52–58 in Table I were synthesized in similar manner, i.e., by condensation of the asymmetric ethylchloroformate acid anhydride with 4(4-piperidyl) 1H-imidazole in the presence of triethyl amine.

Commercially available 3,3-diphenylpropionic acid and 4,4-diphenylbut-3-enoic acid were used as the starting materials for compounds 52 and 54, respectively. The unsaturated alkene bond of 4,4-diphenylbut-3-enoic acid was reduced under mild conditions by Pd/C (5%)/$H_2$ catalysis. This intermediate was then used to synthesize compound 53. Both intermediates 3,3-diclohexylpropionic acid and 4,4-dicyclohexylbutanoic acid, used in the preparation of compounds 55 and 56, respectively, were prepared by reduction of 3,3-diphenylpropionic acid and 4,4-diphenylbutanoic acid in the presence of catalyse Rh/alumina (5%)/$H_2$, 5 atm.

Compound No. 52, yield: 69%; MS.:M/e 359 (M+); $^1$H NMR $CDCl_3$:imidazole H: δ 7.50 and 6.70 (s, 1 H); piperidine H: complex δ 4.60 (d, 2 H), 3.10 (m, 3 H), 2.60 (d, 2 H), 1.40 (m, 2 H); propionyl H: complex δ 3.05 (m, 1 H), 2.00 (d, 2 H); biphenyl H: complex δ 7.20 (m, 10 H), MA.: calc. C=76.85, H=7.00, N=11.68; found, 76.32, 6.72, 10.89, respectively.

Compound No. 53, yield: 73%; MS.:M/e 373 (M+); $^1$H NMR $CDCl_3$:imidazole H: δ 7.65 and 6.70 (s, 1 H); piperidine H: complex δ 4.60 (d, 2 H), 3.00 (m, 2 H), 2.50 (m, 2 H), 1.80 (m, 2 H); butanoyl H: δ 3.05 (m, 2 H), 2.40 (m, 2 H), 3.40 (m, 2 H); diphenyl H: δ 7.10 (m, 10 H).

Compound No. 54, yield: 64%; MS.:M/e 371 (M+); $^1$H NMR $CDCl_3$:imidazole H: δ 7.40 and 6.50 (s, 1 H); piperidyl H: complex δ 4.50 (d, 2 H), 3.60 (m, 3 H), 3.20 (d, 2 H), 1.50 (d, 2 H); butenyl H: complex δ 6.70 (d, 1 H), 3.50 (d, 2 H); diphenyl H:δ 7.10 (m, 10 H).

Compound No. 55, yield: 75%; MS.: M/e 371 (M+); $^1$H NMR $CDCl_3$:imidazole H:δ 8.00 and 7.10 (s, 1 H); piperidyl H: complex δ 4.50 (d, 2 H), 3.10 (d, 2 H), 2.80 (m, 3 H), 1.90 (d, 2 H); propionyl H: complex δ 2.60 (d, 2 H), 2.00 (m, 1 H); dicyclohexyl H: complex δ 1.50 (m, 22 H).

Compound No. 56, yield: 68%; MS.: M/e 385 (M+); $^1$H NMR $CDCl_3$: imidazole H:δ 8.00 and 7.05 (s, 1 H); piperidyl H: complex δ 4.50 (d, 2 H), 3.80 (d, 2 H), 3.00 (m, 3 H) , 2.10 (m, 2 H); butanoyl H: δ complex 2.80 (m, 2 H), 1.80 (m, 2 H), 1.40 (m, 1 H); dicyclohexyl H: complex δ 1.20 (m, 22 H) .

6.1.3. PREPARATION OF 4-(t-BUTOXY CARBONYL-4-PIPERIDYL) 1H-IMIDAZOLE (COMPOUND 2)

To a suspension of 224 mg (1.00 mmol) of 4-(4-piperidyl)-1H-imidazole dihydrochloride in 10 ml of methanol was added 202 mg (2.00 mmol) of triethylamine (the suspension turned to a clear solution) followed by dropwise addition of 218 mg (1.00 mmol) of di-t-butyl dicarbonate in 5 ml methanol over a period of 10 min. The reaction mixture was stirred at 25° C. for 6 h, at the end of which the volatile materials were removed in vacuo. The oily residue was partitioned between 50 ml chloroform and 25 ml water. The organic layer was washed with 50 ml brine solution, then dried over anhydrous sodium sulfate. After filtration and removal of solvent, a pale yellow oil was obtained. The oil was treated with a mixture of methanol: petroleum ether (10:90). The resulting mixture was agitated vigorously with a glass rod until a solid appeared. After filtration and drying, the desired product was obtained as a white power. Yield: 65%; M.P.: 198° C.; MS: m/e 251 (M+); $^1$H NMR ($CDCl_3$): imidazole H: δ 7.60 (s, 1 H) and 6.60 (s, 1 H); piperidine H: δ 4.20 (d, 2 H), 2.80 (m, 4 H), 2.20 (d, 2 H), 1.60 (m, 1 H), t-BOC H: 1.45 (s, 9 H).

Compounds No. 13 and 14 in Table I were synthesized in similar manner. The pure product was obtained by preparative TCL Silica GEL GF, 60 (2000 microns), and the solvent of recrystallization was methanol:anhydrous ether (20:80).

Compound No. 13, yield: 78%; M.P.: 180° C.; MS: m/e 255 (M+); $^1$H NMR ($DMSOd_6$): imidazole H: δ 7.95 and 6.80 (s, 1 H), NH: δ 7.80 and 6.60 (d, 1 H); piperidine H: complex, δ 4.50 (d, 2 H), 3.60 (m, 3 H), 3.10 (m, 1 H), 2.75 (m, 2 H); phenyl H: δ 7.40 (m, 5 H); MA: (C,H,N,): 70.36%, 6.71%, 16.30%.

Compound No. 14, yield: 72%; M.P.: 185° C.; $^1$H NMR ($CDCl_3$); imidazole H: δ 7.60 and 6.80 (s, 1 H); piperidine H: complex, δ 4.50 (d, 2 H), 3.00 (m, 3 H), 2.05 (d, 2 H), 1.60 (m, 2 H); t-butyl H: δ 1.10 (s, 9 H).

6.1.4. PREPARATION OF 4(-4-PIPERIDYL)-1H-IMIDAZOLE

In a preferred embodiment, 4(4-piperidyl)-1H-imidazole for use in the synthesis of the $H_3$-receptors antagonists is prepared according to the following method.

Bromination of 4-acetyl piperidine (Aldrich) in hydrogen bromide/acetic acid was performed as described (Barlin et al., Aust. J. Chem 42:735 (1989)).

A mixture of 11.23 g (4.00 mmol) of bromoacetyl pyridine and 3.98 ml (10.0 mmol) formamide were fused together at 110° C. with stirring for 4 h. The crude reaction mixture was then concentrated on the rotary evaporator to remove volatile matter. The residue was dissolved in 50 ml methanol, and to this solution was added 100 ml anhydrous dimethyl ether slowly with stirring, which led to the formation of a brown precipitate. After stirring for another 0.5 h, the precipitate was filtered, washed with 50 ml anhydrous ether and dried. This solid residue was dissolved in 20 ml water and the aqueous solution was basified to pH 9 with sodium carbonate. To this solution was added 150 ml absolute ethanol slowly with stirring till a solid formed, which was filtered off. The filtrate was heated to boiling, then treated with activated carbon and filtered. The filtrate was concentrated on rotary evaporator to dryness. Yield: 3.36 g 58%; M.P.: 152° C. (decomposed); MS: m/e 145 (M+), $^1$H NMR ($D_2O$): imidazole H: δ 7.80 (s, 1 H) and 7.20 (s, 1 H); pyridyl H: 8.10 (d, 2 H), 7.17 (d, 2 H). The pyridyl moiety was reduced by catalytic hydrogenation using 5–10% rhodium on carbon in acidified water at 20–55 atmospheres as described (Schunack, *Archiv. Pharma.* 306:934 (1973)).

6.2. ANTAGONIST ACTIVITY IN VITRO

The various compounds were tested for the ability to bind to the histamine $H_3$ receptor. A binding assay in a rat brain membrane preparation, based on inhibition of binding of [$^3$H]-N-alpha-methylhistamine using excess unlabeled alpha-methylhistamine to account for nonspecific binding, was developed. Total, specific and nonspecific binding of [$^3$H]-N-alpha-methylhistamine to brain membranes is shown in FIG. 1. The $K_d$ value was 0.19 nM in this preparation and the nonspecific binding was less than 20% of the total binding at the Kd value. The compounds thioperamide (Arrang et al., *Nature* 327:117–123 (1987)) and burimamide (Black et al., *Nature* 236:385–390 (1972)) were tested as controls for this assay. The results are shown in Table I.

TABLE I

4-Piperidyl (imidazole) Compounds and Their Activities on Rat Brain Membranes. $^3$H — N$^\alpha$-methylhistamine as Radioligand)

| Compd No. | R$_1$ | X (=CO—(O)$_x$(CH$_2$)$_n$R) | IC$_{50}$ (nm) | M.P. |
|---|---|---|---|---|
| Thioperamide | H | | 4.0 ± 0.6 | 170° C. |
| | | Burimamide | n = 4 156 ± 57 | |
| 1 | H | —C(=O)—(CH$_2$)$_4$—cyclohexyl | 23 ± 6 n = 3 | 159° |
| 3 | H | —C(=O)—CH$_2$—cyclohexyl | 19 ± 12 n = 3 | Oil |
| 4 | H | —C(=O)—CH$_2$—phenyl | 1400 ± 437 n = 3 | Oil |
| 5 | H | —C(=O)—(CH$_2$)$_3$—phenyl | 262 ± 9 n = 3 | Oil |
| 6 | H | —C(=O)—(CH$_2$)$_2$—cyclohexyl | 34 ± 1.4 n = 3 | Oil |
| 7 | H | —C(=O)—(CH$_2$)$_2$—phenyl | 34.1 ± 3.6 n = 3 | Oil |
| 12 | H | —C(=O)—(CH$_2$)$_3$—cyclohexyl | 41.4 ± 9 n = 3 | 136° C. |
| 13 | H | —C(=O)—phenyl | 151 ± 44 n = 4 | 180° C. |
| 41 | H | —C(=O)—cyclohexyl | inactive n = 2 (1 μM) | 192° C. |
| 42 | CH$_3$ | —C(=O)—phenyl | inactive n = 2 (1 μM) | Oil |
| 43 | X | —C(=O)—phenyl | inactive n = 3 | 99° C. |

TABLE I-continued

4-Piperidyl (imidazole) Compounds and
Their Activities on Rat Brain Membranes.
$^3H-N^\alpha$-methylhistamine as Radioligand)

| # | R | R' | Activity | mp |
|---|---|---|---|---|
| 44 | X | −C(=O)−C(Me)(Me)−Me | inactive, n = 2 | 81° C. |
| 45 | X | −C(=O)−O−C(Me)(Me)−Me | inactive, n = 2 | 79° C. |
| 46 | PhCH₂ | −C(=O)−Ph | inactive, n = 2 | 62° C. |
| 47 | H | −C(=NCN)−O−Ph | 231, n = 1 | 185° C. |
| 48 | H | −C(=NCN)−NH−cyclohexyl | inactive, n = 2 | 168° C. |
| 52 | H | −C(=O)−CH(Ph)(Ph) via CH₂ | 93.1 | 129–131° C. |
| 53 | H | −C(=O)−CH₂−CH(Ph)(Ph) | 124 | oil |
| 54 | H | −C(=O)−CH=C(Ph)(Ph) | 1000 | 158° C. decomp. |
| 55 | H | −C(=O)−CH₂−CH(C₆H₁₁)(C₆H₁₁) | | 118° C. decomp |

TABLE I-continued

4-Piperidyl (imidazole) Compounds and
Their Activities on Rat Brain Membranes.
$^3$H — N$^\alpha$-methylhistamine as Radioligand)

| Cmpd. No. | Structure | IC$_{50}$(Nm) | M.P. |
|---|---|---|---|
| 56 | H ... | | 152° C. decomp. |
| 57 | H ... | | |
| 58 | H ... | | |
| 50 | 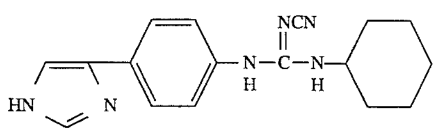 | inactive n = 2 (μM) | 148.5°–150.5° C. |
| 2 | 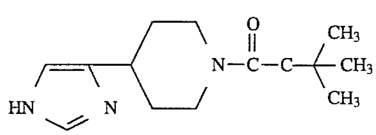 | 243.5 ± 1.9 n = 2 | 198° C. |
| 14 | 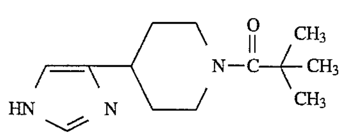 | inactive n = 2 | 185° C. |
| 8 | 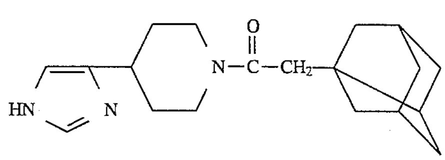 | inactive n = 2 | 151° C. |

TABLE I-continued

4-Piperidyl (imidazole) Compounds and
Their Activities on Rat Brain Membranes.
$^3$H — N$^\alpha$-methylhistamine as Radioligand)

| # | Structure | Activity | Form |
|---|---|---|---|
| 9 | (imidazole-piperidine-N-C(O)-CH(cyclohexyl)$_2$) | inactive, n=2 | 148° C. |
| 10 | (imidazole-piperidine-N-C(O)-CH=CH-phenyl) | 570 ± 172, n=3 | Oil |
| 11 | (imidazole-piperidine-N-C(O)-CH(cyclohexyl)(phenyl)) | 260 ± 38, n=2 | Oil |
| 51 | (imidazole-piperidine-N-C(O)-CH(phenyl)$_2$) |  | 115° C. |

6.3. DISCUSSION

The results in Table I show that the compounds of the invention are effective for binding to the histamine H$_3$-receptor. Interestingly, cyanoguanidine derivatives (e.g., compounds 47, 48 and 50) were ineffective at binding to the H$_3$-receptor. This result is in contrast to earlier observations about H$_2$-receptor antagonists. With H$_2$-receptor antagonists, cyanoguanidine and thiourea-containing derivatives (cimetidine and metiamide, respectively) were found to be bioisosteres, i.e., functionally substantially equivalent (Brimblecombe et al., Gastroenterology 74: 339–347 (1978)).

7. PHARMACOLOGICAL EVALUATION IN THE CNS

A representative compound, 1, was tested in vivo for (1) the ability to penetrate the blood brain barrier; and (2) the effect of behavior in mice.

7.1. PENETRATION OF THE BLOOD-BRAIN BARRIER

Blood-brain barrier penetration in rats was assessed by an ex vivo binding procedure. Young adult male Long-Evans rats were injected i.p. with saline or H$_3$ antagonists in saline. At various times after injection animals were sacrificed, the cortex was removed, homogenized in 50 mM Na/K-phosphate buffer, pH 7.4, and the binding of 1 nM [$^3$H]-N$^\alpha$-methylhistamine was measured using 400 µg protein of the homogenate. Nonspecific binding was accounted for by the inclusion of excess thioperamide in some samples. Under these conditions, the binding was approximately 90% specific.

As shown in FIG. 2, thioperamide at doses of 2, 5, and 10 mg/kg, when measured 15 min after injection, decreased the binding of [$^3$H]-N$^\alpha$-methylhistamine to H$_3$ receptors in the cortex. This means that the thioperamide at these doses and after this time was able to penetrate the blood-brain barrier. FIG. 3 shows that compound 1 also penetrates the blood-brain barrier one hour after injections of doses of 50 and 70 mg/kg. Taking into account the difference in affinity comparing thioperamide (4.0 nM) and compound 1 (23 nM), these data suggest that compound 1 penetrates the blood-brain barrier at least as well as thioperamide.

7.2. BEHAVIORAL EFFECTS IN MICE

The overall strategy to show central nervous system antagonist activity was to challenge effects of the agonist (R)α-methylhistamine. Therefore, the first objective was to establish a dose response curve for behavioral effects of (R)α-methylhistamine. Male albino CF-1 mice weighing 20–30 g were used. Saline or (R)α-methylhistamine in saline was injected i.p. in a volume ≦0.4 ml. Animals were observed for various behaviors three times for 10 seconds during each 10 minute interval for a total of 2 hours. Animals were scored for the presence (1) or absence (0) of the behavior and the results were reported as the accumulated score for a 30 minute period (maximum score=9). As shown in FIG. 4, (R)α-methylhistamine produced a dose-dependent (range of 15 to 35 mg/kg) increase in sleeping one hour after injection. The effect was also evident at 30 minutes after injection.

To assess the effects of antagonists, they were administered with the (R)α-methylhistamine in saline. FIG. 5 shows that thioperamide was able to inhibit the soporific effect of 30 mg/kg of (R)α-methylhistamine. With thioperamide alone (i.e., in the absence of the α-methylhistamine $H_3$ receptor agonist), animals were very active, exhibiting normal behaviors. FIG. 6 shows that compound 1 inhibited the soporific effect of 25 mg/kg (R)α-methylhistamine.

7.3. DISCUSSION

The results of the in vitro (see section 6, supra) and in vivo activity assays show that a compound of the invention is useful for increasing histamine activity in the brain.

In the foregoing in vivo assays, thioperamide was used as a positive control. The results indicate that compound 1 is effective as an $H_3$-receptor antagonist. Direct comparison of the two compounds is not available from the data, however, since the experimental protocols used to test each were not identical.

It is noteworthy that in all testing to date, no toxicity of the 1 compound has been observed, even at high doses.

8. SPECIFICITY OF COMPOUND 1

The selectivity of action of compound 1 for histamine $H_3$-receptors was determined in a NOVASCREEN™ receptor selectivity study. At concentrations of $10^{-5}$ M, no significant binding to adenosine, excitory or inhibitory amino acid, dopamine, serotonin, or a broad range of petidergic receptors, or to ion channel proteins, peptide factor or second messenger systems was observed. The binding study results are shown in Table II.

TABLE II

NOVASCREEN ™ RECEPTOR SELECTIVITY ASSAY

| Receptor/ Selectivity | Reference Compound | Reference $K_i$(nM) | Initial Percent Inhibition (Average; N = 2) $10^{-5}$ M |
|---|---|---|---|
| Adenosine | | | |
| Adenosine | NECA | 120.00 | −3.0 |
| Amino Acids | | | |
| Ecitatory | | | |
| Quisqualate | Quisqualic Acid | 11.80 | −1.8 |
| Kainate | Kainic Acid DME | 24.93 | 42.1 |
| MK-801 | MK801 | 4.30 | −8.6 |
| NMDA | NMDA | 359.00 | −4.5 |
| PCP | PCP | 62.30 | 9.7 |
| Glycine | Glycine | 300.00 | 1.8 |
| Inhibitory | | | |
| Glycine | Strychinine Nitrate | 33.50 | 17.4 |
| $GABA_A$ | GABA | 2.80 | 0.6 |
| $GABA_B$ | GABA | 176.00 | 0.0 |
| Benzodiazephine | Clonazepam | 3.40 | 2.7 |
| Biogenic Amines | | | |
| Dopamine 1 | Butaclamol | 37.30 | 6.4 |
| Dopamine 2 | Spiperone | 0.08 | 3.5 |

TABLE II-continued

NOVASCREEN ™ RECEPTOR SELECTIVITY ASSAY

| Receptor/ Selectivity | Reference Compound | Reference $K_i$(nM) | Initial Percent Inhibition (Average; N = 2) $10^{-5}$ M |
|---|---|---|---|
| Serotonin 1 | Serotonin | 4.60 | −3.6 |
| Serotonin 2 | Serotonin | 531.00 | 10.5 |
| Peptides | | | |
| Angiotensin | Angiotensin II | 0.20 | 6.5 |
| Arg-Vasopressin $V_1$ | arg-Vasopressin | 4.90 | 10.1 |
| Bombesin | Tyr4-Bombesin | 0.55 | −5.5 |
| CCK Central | CCK | 0.13 | 18.6 |
| CCK Peripheral | CCK | 0.02 | 6.9 |
| Substance K | Neurokinin A | 2.75 | 29.2 |
| Substance P | Substance P | 0.08 | 20.0 |
| NPY | Neuropeptide Y | 0.50 | −8.7 |
| Neurotensin | Neurotensin | 1.23 | −10.5 |
| Somatostatin | Somatostatin | 0.03 | 4.1 |
| VIP | VIP | 1.53 | 17.1 |
| Channel Proteins | | | |
| Calcium | w-Conotoxin | 0.01 | 1.9 |
| Calcium | Nifedipine | 1.60 | 8.1 |
| Chloride | TBPS | 112.40 | −3.4 |
| Potassium | Apamin | 0.05 | 7.7 |
| Peptide Factors | | | |
| ANF (rat) | ANP | 0.15 | 0.1 |
| EGF | EGF | 0.24 | 18.1 |
| NGF | NGF | 0.80 | 17.1 |
| Second Messenger Systems | | | |
| Adenylate Cyclase Forskolin | Forskolin | 29.40 | 2.1 |
| Protein Kinase C Phorbol Ester | PDBU | 16.50 | 0.9 |
| Inositol Triphosphate | IP3 | 12.50 | 9.2 |

Values are expressed as the percent inhibition of specific binding and represent the average of duplicate tubes at each of the concentrations tested. Bolded values represent inhibition of fifty percent or greater.

9. DEMONSTRATION OF APPETITE SUPPRESSION ACTIVITY IN VIVO

Male Sprague-Dawley rats (200–300 grams) were used in all experiments. Rats were fasted for 24 hours prior to all experiments. Water was provided ad lib. Rats were singly placed in a ventilated plastic circular rat metabolism chamber with a stainless steel wire mess grid flood equipped with food and $H_2O$ attachments. A measured quantity of food (50 grams) and water (100 mls) was supplied through attachments to the metabolism chambers. Food and water intake was measured at the 2, 4 and 6 hour time periods.

Immediately prior to placement of the rats in the metabolism chambers, animals were administered interperitoneally, vehicle or compound 1 (3, 10 or 30 mg/kg). Final volumes were 1.0 ml/kg. Subsequently, they were left undisturbed for the experimental period except when the food and $H_2O$ attachments were briefly removed for measurement of food and water intake. At the completion of the experiment, animals were returned to their home cages. The results are found in Table III and FIGS. 7 and 8.

TABLE III

| | | The Effect of Food Intake In Rats Following The Administration of Compound I | | |
|---|---|---|---|---|
| | Column 1 | 2 HR S.E. | 4 HR S.E. | 6 HR S.E. |
| 1 | VEHICLE | 6.167 ± 0.366 | 7.083 ± 0.358 | 13.000 |
| 2 | 3 mg/kg | 5.687 ± 0.494 | 7.333 ± 0.558 | |
| 3 | 10 mg/kg | 2.000 ± 0.258 | 5.167 ± 0.601 | |
| 4 | 30 mg/kg | 1.167 ± 0.477 | 2.333 ± 0.615 | 5.000 ± 0.940 |

The above protocol is repeated for the histamine $H_3$ receptor antagonists disclosed herein.

The present invention is not to be limited in scope by the specific embodiments described herein. Indeed, various modifications of the invention in addition to those described herein will become apparent to those skilled in the art from the foregoing description and accompanying figures. Such modifications are intended to fall within the scope of the appended claims.

Various publications are cited herein, the disclosures of which are incorporated by reference in their entireties.

What is claimed is:

1. A method of suppressing appetite in a subject comprising administering to an animal, in whom appetite suppression is desired, an effective amount of a compound of the formula:

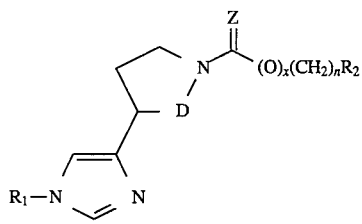

I wherein $R_1$ represents hydrogen, an in vivo hydrolyzable group, an alkyl group., a cyclic alkyl group, or an aryl group; D is $CH_2$ or $C_2CH_2$; Z is S or O; x is 0 or 1; n is an integer from 0 to 6; and $R_2$ represents a substituted or unsubstituted linear chain or branched chain alkyl group of up to about 20 carbon atoms, a substituted or unsubstituted carbocyclic group of up to about 20 atoms, or a substituted or unsubstituted aryl group of up to about 20 carbon atoms, and salts thereof, with the provisos that if $R_2$ is tert-butyl, cyclohexyl, or dicyclohexylmethyl, x or n must not be 0; and if $R_2$ is adamantane, the sum of x and n must be greater than 1;. or a pharmaceutically acceptable salt thereof.

2. The method according to claim 1 in which the animal is human, and said administration is to treat obesity or weight gain.

3. A method of suppressing appetite in an animal comprising administering to an animal, in whom appetite suppression is desired, an effective amount of a compound of the formula:

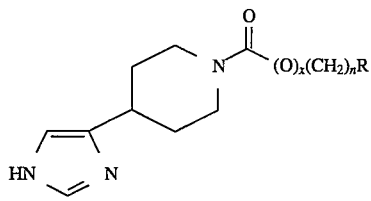

II wherein x is 0 or 1; n is an integer from 0 to 6; and R represents a substituted or unsubstituted linear chain or branched chain alkyl group of up to about 20 carbon atoms, a substituted or unsubstituted carbocyclic group of up to about 20 carbon atoms, or substituted or unsubstituted aryl group of up to about 20 carbon atoms, and salts thereof, with the provisos that if R is tert-butyl, cyclohexyl, or dicyclohexylmethyl, x or n must not be 0; and if R is adamantane, the sum of x and n must be greater than 1; or a pharmaceutically acceptable salt thereof.

4. A method of suppressing appetite in an animal comprising administering to an animal, in whom appetite suppression is desired, an effective amount of a compound of the formula:

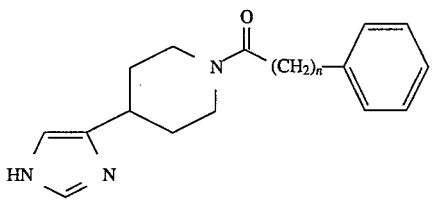

wherein n is 0, 1, 2, 3 or 4; or a pharmaceutically acceptable salt thereof.

5. A method of suppressing appetite in an animal comprising administering to an animal, in whom appetite suppression is desired, an effective amount of a compound of the formula:

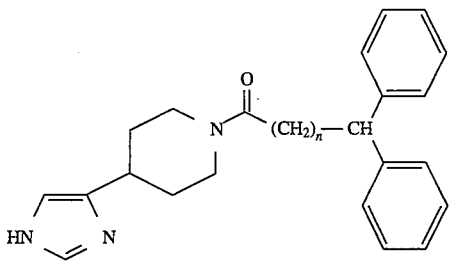

in which n is 1, 2, 3 or 4; or a pharmaceutically acceptable salt thereof.

6. A method of suppressing appetite in an animal comprising administering to an animal, in whom appetite suppression is desired, an effective amount of a compound of the formula

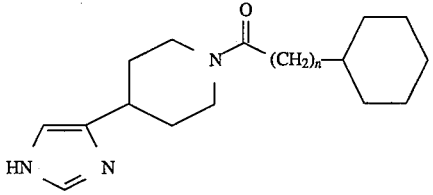

in which n is 1, 2, 3 or 4; or a pharmaceutically acceptable salt thereof.

7. The method according to claim 1, 3, 4, 5, 6 or 2 wherein said compound is administered orally.

8. The method according to claim 1, 3, 4, 5, 6or 2 wherein said compound is administered by intravenous, intramuscular, intraperitoneal, or subcutaneous injection.

9. The method according to claim 1, 3, 4, 5, 6 or 2 wherein the amount of said compound administered is about 0.01 mg/kg to about 200 mg/kg in a single dose or divided dose per day.

* * * * *